US011051864B2

(12) United States Patent
Appenzeller et al.

(10) Patent No.: US 11,051,864 B2
(45) Date of Patent: Jul. 6, 2021

(54) INTRAMEDULLARY FIXATION ASSEMBLY

(71) Applicant: DePuy Synthes Products, Inc., Raynham, MA (US)

(72) Inventors: Andreas Appenzeller, Oberdorf (CH); Ladislav Nagy, Kilchberg (CH); Daniel Fluri, Oberdorf (CH); Christof Dutoit, Oberdorf (CH); Andre Galm, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 892 days.

(21) Appl. No.: 13/793,044

(22) Filed: Mar. 11, 2013

(65) Prior Publication Data

US 2014/0066932 A1 Mar. 6, 2014

Related U.S. Application Data

(60) Provisional application No. 61/723,016, filed on Nov. 6, 2012, provisional application No. 61/695,254, filed on Aug. 30, 2012.

(51) Int. Cl.
*A61B 17/72* (2006.01)
*A61B 17/17* (2006.01)

(52) U.S. Cl.
CPC .......... *A61B 17/72* (2013.01); *A61B 17/1725* (2013.01); *A61B 17/7233* (2013.01)

(58) Field of Classification Search
CPC .. A61B 17/72; A61B 17/1725; A61B 17/7233
USPC .................................................. 606/62–68
See application file for complete search history.

(56) References Cited

U.S. PATENT DOCUMENTS

| 2,998,007 | A | * | 8/1961 | Herzog | 606/63 |
| 4,011,863 | A | * | 3/1977 | Zickel | 606/299 |
| 4,503,847 | A | * | 3/1985 | Mouradian | 606/64 |
| 5,035,697 | A | | 7/1991 | Frigg | |

(Continued)

FOREIGN PATENT DOCUMENTS

| DE | 000010201743 | 8/2003 |
| EP | 0086552 | 8/1983 |

(Continued)

OTHER PUBLICATIONS

International Patent Application No. PCT/US2013/056356: International Search Report dated Oct. 31, 2013, 13 pages.

(Continued)

*Primary Examiner* — Jacqueline T Johanas
(74) *Attorney, Agent, or Firm* — Fay Kaplun & Marcin, LLP

(57) ABSTRACT

Intramedullary fixation assemblies (4, 8) and intramedullary fixation devices (1, 24) can be used in orthopaedic surgery for the fixation of bone fractures. Also disclosed is an insertion device (30) for inserting an intramedullary fixation device, and a method of fixing a bone fracture. The fixation devices are preferably for addressing fractures of the distal radius, and are preferably styloid nails. The styloid nails preferably have a head portion that can accept up to three bone screws; one of the bone screws is designed to extend across a fracture line between a proximal and a distal bone fragment while the other bone screws are designed to be retained in the distal bone fragment.

18 Claims, 18 Drawing Sheets

(56) References Cited

U.S. PATENT DOCUMENTS

| | | | |
|---|---|---|---|
| 5,041,115 A | 8/1991 | Frigg et al. | |
| 5,176,681 A | 1/1993 | Lawes et al. | |
| 5,603,715 A * | 2/1997 | Kessler | 606/63 |
| 5,658,288 A | 8/1997 | Kim | |
| 5,697,930 A | 12/1997 | Itoman et al. | |
| 5,814,047 A | 9/1998 | Emilio et al. | |
| 6,210,414 B1 * | 4/2001 | Lin | 606/64 |
| 6,270,499 B1 | 8/2001 | Leu et al. | |
| 6,527,775 B1 | 3/2003 | Warburton | |
| 6,629,976 B1 | 10/2003 | Gnos et al. | |
| 6,660,009 B1 | 12/2003 | Azar | |
| 6,706,046 B2 | 3/2004 | Orbay et al. | |
| 6,730,090 B2 | 5/2004 | Orbay et al. | |
| 6,793,659 B2 | 9/2004 | Putnam | |
| 7,160,302 B2 | 1/2007 | Warburton | |
| 7,713,271 B2 | 5/2010 | Warburton | |
| 7,727,264 B2 | 6/2010 | Orbay et al. | |
| 7,854,767 B2 * | 12/2010 | May et al. | 623/18.11 |
| 8,092,453 B2 | 1/2012 | Warburton | |
| 8,100,910 B2 | 1/2012 | Warburton | |
| 8,287,538 B2 * | 10/2012 | Brenzel et al. | 606/62 |
| 8,439,917 B2 * | 5/2013 | Saravia et al. | 606/66 |
| 8,906,022 B2 * | 12/2014 | Krinke et al. | 606/63 |
| 8,961,516 B2 * | 2/2015 | Nelson et al. | 606/64 |
| 2003/0083661 A1 * | 5/2003 | Orbay et al. | 606/69 |
| 2004/0049192 A1 * | 3/2004 | Shimizu | 606/62 |
| 2005/0015154 A1 * | 1/2005 | Lindsey et al. | 623/23.46 |
| 2005/0283154 A1 * | 12/2005 | Orbay et al. | 606/62 |
| 2006/0015101 A1 | 1/2006 | Warburton | |
| 2006/0100624 A1 * | 5/2006 | Orbay et al. | 606/69 |
| 2006/0200143 A1 * | 9/2006 | Warburton | 606/62 |
| 2006/0200157 A1 * | 9/2006 | Orbay et al. | 606/87 |
| 2007/0083202 A1 * | 4/2007 | Eli Running et al. | 606/62 |
| 2007/0191855 A1 | 8/2007 | Orbay | |
| 2008/0208261 A1 * | 8/2008 | Medoff | 606/280 |
| 2008/0269749 A1 * | 10/2008 | Shalaby et al. | 606/62 |
| 2008/0269776 A1 * | 10/2008 | Justin et al. | 606/129 |
| 2009/0157077 A1 * | 6/2009 | Larsen et al. | 606/62 |
| 2009/0157079 A1 * | 6/2009 | Warburton et al. | 606/62 |
| 2009/0182336 A1 * | 7/2009 | Brenzel et al. | 606/62 |
| 2009/0292292 A1 * | 11/2009 | Fencl et al. | 606/104 |
| 2010/0268229 A1 * | 10/2010 | Siravo et al. | 606/64 |
| 2010/0292722 A1 * | 11/2010 | Klaue | 606/167 |
| 2010/0305623 A1 * | 12/2010 | Klaue | 606/329 |
| 2011/0087227 A1 * | 4/2011 | Mazur et al. | 606/62 |
| 2011/0137312 A1 * | 6/2011 | Mantovani et al. | 606/63 |
| 2011/0178520 A1 * | 7/2011 | Taylor et al. | 606/62 |
| 2011/0213367 A1 * | 9/2011 | Tyber et al. | 606/62 |
| 2011/0230884 A1 * | 9/2011 | Mantzaris et al. | 606/64 |
| 2012/0130370 A1 * | 5/2012 | Kinmon | 606/62 |
| 2012/0245642 A1 * | 9/2012 | Giannoudis et al. | 606/280 |
| 2013/0116693 A1 * | 5/2013 | Nelson et al. | 606/64 |
| 2013/0231665 A1 * | 9/2013 | Saravia et al. | 606/63 |
| 2014/0142575 A1 * | 5/2014 | Biedermann et al. | 606/62 |

FOREIGN PATENT DOCUMENTS

| | | |
|---|---|---|
| EP | 0202141 | 11/1986 |
| EP | 0355411 | 2/1990 |
| EP | 1330988 | 7/2003 |
| EP | 1808143 | 7/2007 |
| WO | WO 99/0035989 | 7/1999 |
| WO | WO 02/24088 | 3/2002 |

OTHER PUBLICATIONS

Minimally Invasive Dorsal Endoplate, Surgical Technique for the DNP Plate, Hand Innovations, www.orthopaediclist.com, posted Apr. 19, 2005; 14 pages.

* cited by examiner

INTRAMEDULLARY FIXATION ASSEMBLY

CROSS REFERENCE TO RELATED APPLICATIONS

This application claims the benefit of U.S. Provisional Patent Application Ser. No. 61/695,254 filed Aug. 30, 2012 and Application Ser. No. 61/723,016 filed Nov. 6, 2012, the contents of which are hereby incorporated by reference herein in their entirety.

TECHNICAL FIELD

The present disclosure relates to intramedullary fixation devices, methods for fixing bone fractures and devices for inserting intramedullary fixation devices.

BACKGROUND

The use of intramedullary fixation devices to fix bone fractures is well known in the orthopaedic field. With those nails known in the art, a surgeon will have to make multiple skin incisions, and drill multiple bone holes in order to implant the nails. This results in a long, complicated procedure requiring multiple instruments and resulting in multiple traumas to the patient.

Also, WO 02/024088 discloses an intramedullary interlocking fixation rod to fix a bone fracture comprising an intramedullary nail which requires anchoring of its head by a screw in the articular fragment of the bone and anchoring of its tail in the medullary canal of the second fragment of the bone with two further screws. Due to the requirement of screws at multiple positions on the fixation rod, multiple skin incisions and bone holes are required for insertion of the nail.

There is therefore a need in the art for nail devices for fixing bone fractures that require fewer skin incisions, fewer bone holes and that do not require a multitude of instruments for implantation.

SUMMARY

In a first aspect, an intramedullary fixation assembly can include an intramedullary fixation device, such as an intramedullary nail, and at least one fixation element, such as a plurality of fixation elements. The intramedullary fixation device can be dimensioned to lie in a medullary canal of a bone when implanted, the intramedullary nail including:
 a head from which a shaft extends defining an insertion axis, and
 a body, and plurality of insertion channels arranged through the body, the insertion channels configured to receive the fixation elements, respectively, therethrough, each insertion channel defining an insertion point, an exit point and a channel axis passing through the insertion point and the exit point;

The head may comprise an insertion area in which each insertion point of the plurality of insertions channels is located. The insertion area may be dimensioned and positioned to remain accessible through a hole in a bone through which the intramedullary nail has been inserted.

The intramedullary fixation device may be completely inserted and fixed in position through a single hole in a bone. Fixation of the intramedullary fixation device is possible with only a single skin incision and through the making of a single bone hole. Additional locking of the end of the intramedullary fixation device opposed to the insertion area is unnecessary.

All insertion channels of the intramedullary fixation device may have their insertion points located in the insertion area.

The insertion area may be the only area in the nail having insertion points through which fixation elements can be inserted.

The insertion axis and each of the plurality of channel axes may diverge with respect to each other away from the insertion area. The insertion axis and plurality of channel axes pyramidally may diverge with respect to each from the insertion area.

The plurality of insertion channels may include, and can be limited to, two insertion channels. When implanted, one of the insertion axis or one of the channel axes of the two insertion channels may extend in a direction from a first bone fragment to a second bone fragment, the bone fragments separated by a fracture, and the other two of the insertion axis and the channel axes of the two insertion channels may extend within the first bone fragment.

Alternatively, the plurality of insertion channels may include, and can be limited to, three insertion channels. When implanted, two of the insertion axis or the channel axes of the three insertion channels may extend in a direction from a first bone fragment to a second bone fragment, the bone fragments separated by a fracture, and the other two of the insertion axis and the channel axes of the three insertion channels may extend within the first bone fragment.

The intramedullary fixation assembly, including the intramedullary fixation device and the fixation elements, may restrict motion in up to six dimensions and have the effect of ensuring that the bone fracture is stably reduced and thereby supporting bone healing. In particular, the combination of the intramedullary nail and the three insertion channels has the effect of restricting motion in six dimensions.

One of the channel axes may be a coaxial channel axis. A portion of the coaxial channel axis may be substantially coaxial with the insertion axis. The intramedullary fixation device can include a body, and the insertion channel having the coaxial channel axis may run through the body of the intramedullary fixation device from its insertion point to its exit point, the exit point being located in the shaft. The insertion axis may curve away from the coaxial channel axis in the vicinity of the exit point in a direction from the exit point to the end of the shaft.

At least one of the plurality of insertion channels may have a seating area configured to locking hold a portion of a fixation element therein. The seating area may be located adjacent an insertion point of one of the plurality of insertion channels, said one of the plurality of insertion channels has its exit point located in the shaft. Each one of the plurality of insertion channels may have a seating area configured to locking hold a portion of a fixation element therein, each seating area located adjacent respective insertion points.

The intramedullary fixation device can include a body, which can be a nail body (for instance, when the intramedullary fixation device is an intramedullary nail such as a styloid nail) that can have a curvilinear shape and the shaft may be configured to be elastically deformable to conform to the shape of the medullary canal during implantation. The shaft of the nail body can be substantially smooth and devoid of threads.

The shaft of the body of the intramedullary fixation device may body be threaded.

The head may be shaped to reside within a head of a long bone, such as the styloid region of a long bone.

The head may be dimensioned to reside within a head of a long bone, such as the styloid region of a long bone.

The intramedullary fixation assembly can include the intramedullary fixation device, which can be a styloid nail device, for fixing a bone fracture. The styloid nail device may comprise a first longitudinal fixation element configured to pass across the fracture line between a first bone fragment and a second bone fragment. The intramedullary fixation assembly can further include a plurality of second fixation elements configured to anchor the styloid nail device in the first bone fragment.

The head of the first longitudinal fixation element may be configured to accommodate the plurality of second fixation elements further, and one of the second fixation elements may be configured to pass from a distal bone fragment to a proximal bone fragment.

The first longitudinal fixation element may be flexible and bowed. This may improve the anchoring of the styloid nail device in the medullary canal of the bone.

As used herein, a distal bone fragment is the fragment of a fractured bone in which the fracture line is closest to a joint. For example, the distal fragment is an articular bone fragment, and the fracture may be an extra articular fracture. An extra articular fracture is a fracture where the bone has not penetrated the skin, contains only one complete fracture line, and the fracture line does not intersect with part of the joint.

The second fixation elements may be screws or staples which have a longitudinal core. The longitudinal cores of the second fixation elements, and also the first fixation element, may be identical. Having fixation elements with the same core diameter provides the advantage that a reduced number of instruments are needed for implantation of the intramedullary fixation assembly (as compared to an assembly comprising elements with differing diameters), thereby reducing the complexity and costs of the implantation procedure.

As used herein, the "core" of a screw refers to the longitudinal shaft of the screw upon which the thread resides.

The intramedullary fixation assembly may have at least three second fixation elements, which may be screws, wherein the second fixation elements are mounted in the head of the first longitudinal fixation element so as to form a pyramidal engagement with a bone fragment. The pyramidal engagement prevents all rotation and separation of the bone fragments, with the exception of micromovements. Therefore, a stable fixation of the bone can be achieved, whilst minimal instrumentation is needed to insert the styloid nail device and minimal trauma is caused to the patient as few incisions in the skin and bone holes are required.

The head of the longitudinal first fixation element may have holes that are threaded to receive the second fixation elements. Advantageously, this increases the stability of the intramedullary fixation device.

The intramedullary fixation device may be an intramedullary nail or screw. The term "intramedullary" is known in the art and denotes that the nail resides at least partly in the medullary canal of the bone.

Two of the second fixation elements may be screws configured to be located in a distal bone fragment, and a tail of a third second fixation element is configured to pass from the distal bone fragment to a proximal bone fragment across a fracture line, and wherein at least a portion of the second fixation element that crosses the fracture line is configured to extend longitudinally through the first fixation element.

The advantage associated with this particular configuration, especially where the second fixation elements form a pyramidal engagement with the bone fragment, is that a stable fixation of the bone is achieved with the requirement of only one skin incision and one bone hole to implant the styloid nail device.

In a second aspect, an intramedullary fixation device can be pass from a first bone fragment to a second bone fragment across a fracture line, wherein the intramedullary fixation device is threaded. Further, the second aspect also provides an intramedullary fixation assembly that includes the intramedullary fixation device and a first fixation element, wherein the intramedullary fixation device is adapted to be received in a head of the first fixation element, such that the intramedullary fixation device can be anchored in a distal bone fragment, wherein the head of the first fixation element is adapted to further accommodate a plurality of second fixation elements.

At least one of the second fixation elements of the second aspect may be configured to pass between a first bone fragment and a second bone fragment across a fracture line, in use.

The first and second fixation elements of the second aspect may be screws which may have longitudinal cores, which may have the same core diameter. As with the first aspect, this has the advantage that less instrumentation is required for implantation.

In a third aspect, an intramedullary fixation assembly may have an intramedullary fixation device having a body dimensioned to lie in a medullary canal of a bone when implanted, the body having:
  a head from which a shaft extends;
  a first insertion channel for receiving a fixation element therethrough, the first insertion channel defining an insertion point and an exit point, and
  a second insertion channel for receiving a fixation element therethrough, the second insertion channel defining an insertion point and an exit point.

The head may comprise an insertion area in which the insertion points of the first and second insertions channels are located. The insertion area may be dimensioned and positioned to remain accessible through a hole in a bone through which the nail body has been inserted.

The intramedullary fixation assembly also has a first fixation element for insertion in the insertion point of the first insertion channel and a second fixation element for insertion in the insertion point of the second insertion channel.

When implanted at least one of the shaft, the first fixation element and the second fixation element is a bridging element arranged to span across a bone fracture from a first bone fragment to a second bone fragment, and thus is an intramedullary fixation device, and at least one of the shaft, the first fixation element and the second fixation element is arranged to lie within the first bone fragment.

The intramedullary fixation assembly of the third aspect has a bridging element for allowing a second bone fragment to be fixed to a first bone fragment through insertion of the bridging element in the vicinity of a single bone hole.

A fixation element separate from the intramedullary fixation assembly may be additionally inserted from the first to the second bone fragment to lock the bone fragments together and restrict motion in six dimensions.

The bridging element may have a multi-faceted outer surface for engaging with a medullary canal of the first and second bone fragments.

The body of the intramedullary fixation device, which can be a nail, may have a third insertion channel for receiving a fixation element therethrough. The third insertion channel may define an insertion point and an exit point. The head may have an insertion area in which the insertion points of the first, second and third insertions channels are located. The insertion area may be dimensioned and positioned to remain accessible through a hole in a bone through which the nail body has been inserted. The intramedullary fixation assembly may have a third fixation element. When implanted two of the shaft and the first, second and third fixation elements may be bridging elements and the other two of the shaft and the first, second and third fixation elements may lie within the first bone fragment.

The intramedullary nail may be inserted in a minimally invasive manner through a single incision in skin, and other soft tissue, and through making a single hole in a bone to be fixated. The combination of the intramedullary nail and first through third fixation elements lock the second bone fragment to the first bone fragment and restrict motion in six dimensions to support bone healing using minimally invasive techniques.

The insertion paths may be defined by the shaft and the plurality of insertion channels pyramidally diverging with respect to each other from the insertion area.

The fixation elements may form a pyramidal engagement with the bone, the angle between the elements at the vertex of the pyramid at the insertion area on the head of the intramedullary nail may all be different or equal and may be 109.5°, or 100°, or 90°, or 80°, or 70°, or 60°. There may be a pair of fixation elements in which the angle between them at the vertex of the pyramid is, for example 60° and the third fixation element is at an angle of 100° from each of the pair of fixation elements. For example, in aspect one, the third second fixation element (that may cross the bone fracture), is at an angle of about 100° from the second fixation elements that remain in the distal fragment of the bone, and the second fixation elements that remain in the distal fragment of the bone are at an angle of about 60°.

The insertion channels may be configured according to the type of fixation element they are to receive. The fixation elements may be, but are not limited to, being one of a locking screw, a variable angle locking screw or a staple.

The intramedullary nail of the third aspect may have any of the features of the intramedullary nail of the first aspect.

In a fourth aspect, an intramedullary fixation system may include an intramedullary fixation device according to the first aspect or the second aspect. The intramedullary fixation system also has an aiming arm. The aiming arm may be connectable to the intramedullary nail and may define a plurality of guide channels therein. Each guide channel may have a guide axis aligned with a respective channel axis of an insertion channel, the channel axes diverging from an insertion area defined in a head of the intramedullary nail.

The intramedullary fixation system may further include a measuring device for measuring the depth of insertion of a fixation element.

The aiming arm may include, consist of or consist essentially of a radiolucent material. The radiolucent material is polyether ether ketone (PEEK). The aiming arm may have an x-ray visible mark.

In a fifth aspect, a first fixation element can be adapted to receive an intramedullary fixation device, such that the intramedullary fixation device can pass across a bone fracture between a first bone fragment and a second bone fragment in use, the first fixation element being threaded to anchor the first fixation element in a first bone fragment, a head of the first fixation element being further shaped to receive at least one second fixation element. The head of the first fixation element may be threaded to receive the second fixation element.

The head of the fixation element of the fifth aspect may be shaped to accommodate second fixation elements such that they define a pyramidal anchor. The advantage associated with this particular configuration, especially where the second fixation elements form a pyramidal engagement with the bone fragment, is that a stable fixation of the bone is achieved with the requirement of only one skin incision and one bone hole to implant the styloid nail device.

The intramedullary fixation devices, including styloid nail devices, styloid nails, and fixation elements described herein may be used in the temporal bone of the skull, and the ulna, tibia and fibula styloid processes, or any suitable alternative long bone as desired. In particular, intramedullary fixation devices, including styloid nail devices, styloid nails, and fixation elements described herein are used to fix an extraarticular fracture of the distal radius, and are inserted through the styloid process of the distal radius.

The term "styloid process" is a term known in the art and refers to a projection of bone on the surface of a bone, that serves as a small attachment point for muscles.

The head of the first fixation element may have holes that are threaded to receive the intramedullary fixation device and second fixation elements. Advantageously, this increases the stability of the combination.

In a sixth aspect, a method of implanting an intramedullary fixation device in a medullary canal of a bone cam support bone healing of a bone fracture between a first bone fragment and a second bone fragment. The method may have the steps of:

aligning the first and second bone fragments;
  making a hole in the cortical bone of the first bone fragment;
  passing an intramedullary fixation device through the hole, the intramedullary fixation device having a head from which a shaft extends and a plurality of fixation element receiving channels, each one of the plurality of fixation element receiving channels having an insertion point located in an insertion area defined in the head;
  inserting a first fixation element through an insertion point in the insertion area; and
  inserting a second fixation element through a different insertion point in the insertion area.

At least one of the shaft, the first fixation element and the second fixation element so inserted may be a bridging element arranged to span from the first bone fragment to the second bone fragment across the bone fracture and at least one of the shaft, the first fixation element and the second fixation element is arranged to lie within the first bone fragment.

A measurement may be taken before insertion of each of the first and the second fixation elements for determining the length of the fixation element to be inserted.

The first and second fixation elements may have the same core diameter.

The shaft may be threaded.

The fixation elements may be inserted in a manner so as to form a stable pyramidal construct with the bone.

The first bone fragment may be an articular fragment.

The fracture may be an extraarticular fracture.

In a seventh aspect, a method of fixing a bone fracture comprises making a single skin incision. The advantages associated with an implantation that only requires a single skin incision will be recognised by those skilled in the art.

For example, minimal trauma is caused to the patient therefore minimising healing time and minimising the possibility of complications resulting from the procedure. The method may further comprise making only a single bone hole, with the same advantages associated with a single skin incision.

The method of fixing a bone fracture may comprise i) making one skin incision, ii) drilling a hole in a distal fragment of the bone; iii) inserting a first fixation element into the distal bone fragment; iv) inserting at least one second fixation element into the distal bone fragment.

The first fixation element of the method may be inserted so as to pass from the distal bone fragment to the proximal bone fragment across a fracture line, and the second fixation element may be inserted through the first fixation element. This insertion may be through the head of the first fixation element and the second fixation element may be inserted so as to remain entirely in the distal bone fragment.

A measurement may be taken before the second fixation element is inserted. This measurement is used to determine the length required of the at least one second fixation element.

A further second fixation element may be inserted through the head of the first fixation element in a manner so as to pass from a distal bone fragment across a fracture line to a proximal bone fragment.

The advantage associated with this method is that a stable fixation can be achieved with only a single skin incision and single bone hole. Advantageously, this method may be carried out using the device for inserting an intramedullary fixation device of the type described herein. Therefore, a stable fixation of the bone is achieved using minimal instrumentation.

The method of fixing a bone fracture may comprise, i) making an incision in the skin; ii) inserting a wire in a distal bone fragment, substantially parallel to a joint in the distal fragment; iii) measuring a depth of the distal bone fragment; iv) drilling a hole in a distal bone fragment substantially parallel to a joint in the distal fragment; v) placing a screw in the hole drilled in the bone fragment; vi) drilling one or more further holes in the distal fragment; viii) inserting one or more screws in the distal fragment, at least one of which passes from the distal bone fragment to a proximal bone fragment across a fracture line.

The fixation elements may be inserted so as to form a stable pyramidal construct with the bone, with the advantages previously discussed for this type of construct.

The depth of the distal bone fragment may be measured by applying a measuring device to the wire inserted in the distal bone fragment, which is calibrated with the length of wire employed. The wire may have a diameter of 1.1 mm, and may be a K-wire, and where the bone is the radius, the wire may be inserted into the volar-ulnar canal.

As used herein, K-wire is a shortened form of Kirschner wire, a sterilised, sharpened, smooth stainless steel pin used widely in the orthopaedic art.

The hole in the distal bone fragment may be drilled by applying a drill over the inserted wire, the drill may have a diameter of 2.0 mm.

The screw may be inserted over the guide wire, after which point the guide wire is removed.

Before drilling one or more further holes in the distal fragment, a second guide wire, which may be a 1.1 mm K-wire, may be inserted. The drilling of the one or more further holes may then be performed over the second guide wire. A measurement may then be taken to measure the length required for the one or more screws in the distal fragment, by applying a measuring device to the second guide wire. The one or more screws may then be inserted over the guide wire, before removal of the guide wire.

The one or more further screws that pass from the distal bone fragment to a proximal bone fragment across a fracture line may be inserted over a guide wire, which may be a 1.1 mm K-wire, after a hole has been drilled from the distal bone fragment to the proximal bone fragment across the fracture line, wherein the hole was drilled over the guide wire.

The advantage of this method is that a stable fixation can be achieved with the use of minimal instrumentation.

In an eighth aspect, an insertion device is provided and is configured to insert an intramedullary fixation device in a bone having a fracture, the device comprising; i) a first part configured to insert a first fixation element longitudinally through a distal fragment of the bone and across a fracture line; ii) an aiming arm configured to insert a guide wire; and iii) a measuring device for measuring the depth of insertion of the guide wire.

Advantageously, the device for inserting an intramedullary fixation assembly can be used with certain aspects of the method of fixing a bone fracture.

The device of the eighth aspect may be configured to insert one or more second fixation elements into the distal fragment of the bone, through a head of the first fixation element. The device may be configured to insert the one or more second fixation elements via the aiming arm.

The device of the eighth aspect includes, consists of or consists essentially of a radiolucent material which may be polyether ether ketone. Advantageously, this allows the surgeon using the device to have a clear view of the wires, screws and nails being used in the device via x-ray imaging. The device may have an x-ray visible mark on the aiming arm, to help the surgeon aim the guide wire.

As used herein, radiolucent refers to a material that allows the passage of x-rays with little attenuation, thereby rendering the material not visible by x-ray imaging.

Advantageously, the device of the eighth aspect can be used to insert a styloid nail device which provides a stable construct in the bone, preventing all rotation and separation of the bone fragments (except micromovements), with only one skin incision and one bone hole. Minimal instrumentation is also required.

The intramedullary fixation assemblies, including the intramedullary fixation devices, may be used in the temporal bone of the skull, and the ulna, tibia and fibula styloid processes, or in any suitable alternative long bone.

BRIEF DESCRIPTION OF THE DRAWINGS

Embodiments will now be described in detail with reference to the accompanying drawings, in which.

DETAILED DESCRIPTION

Figure 1A:
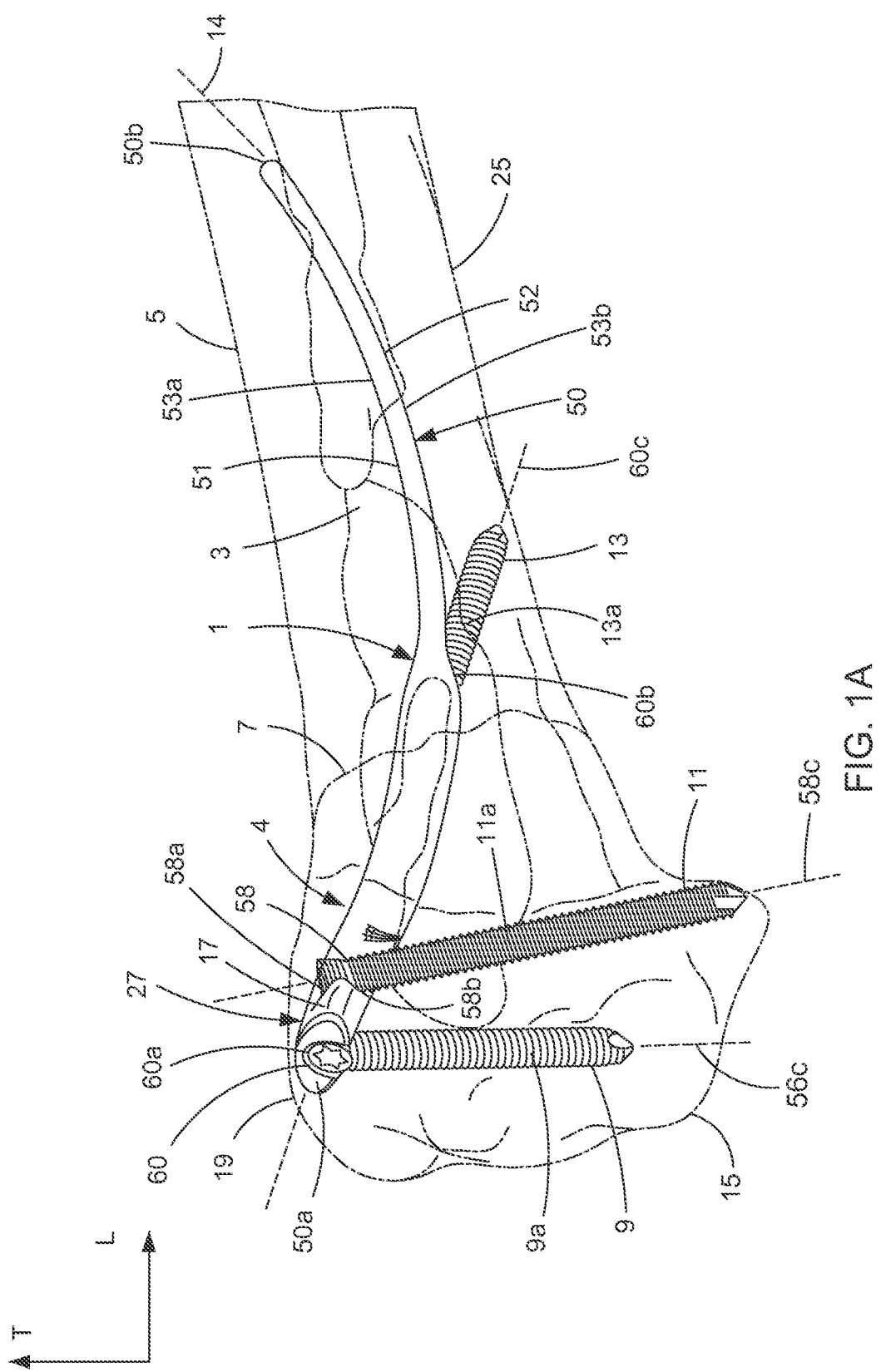
FIG. 1A is a perspective view of an intramedullary fixation assembly in accordance with one embodiment, shown implanted into a bone.
Figure 1B:
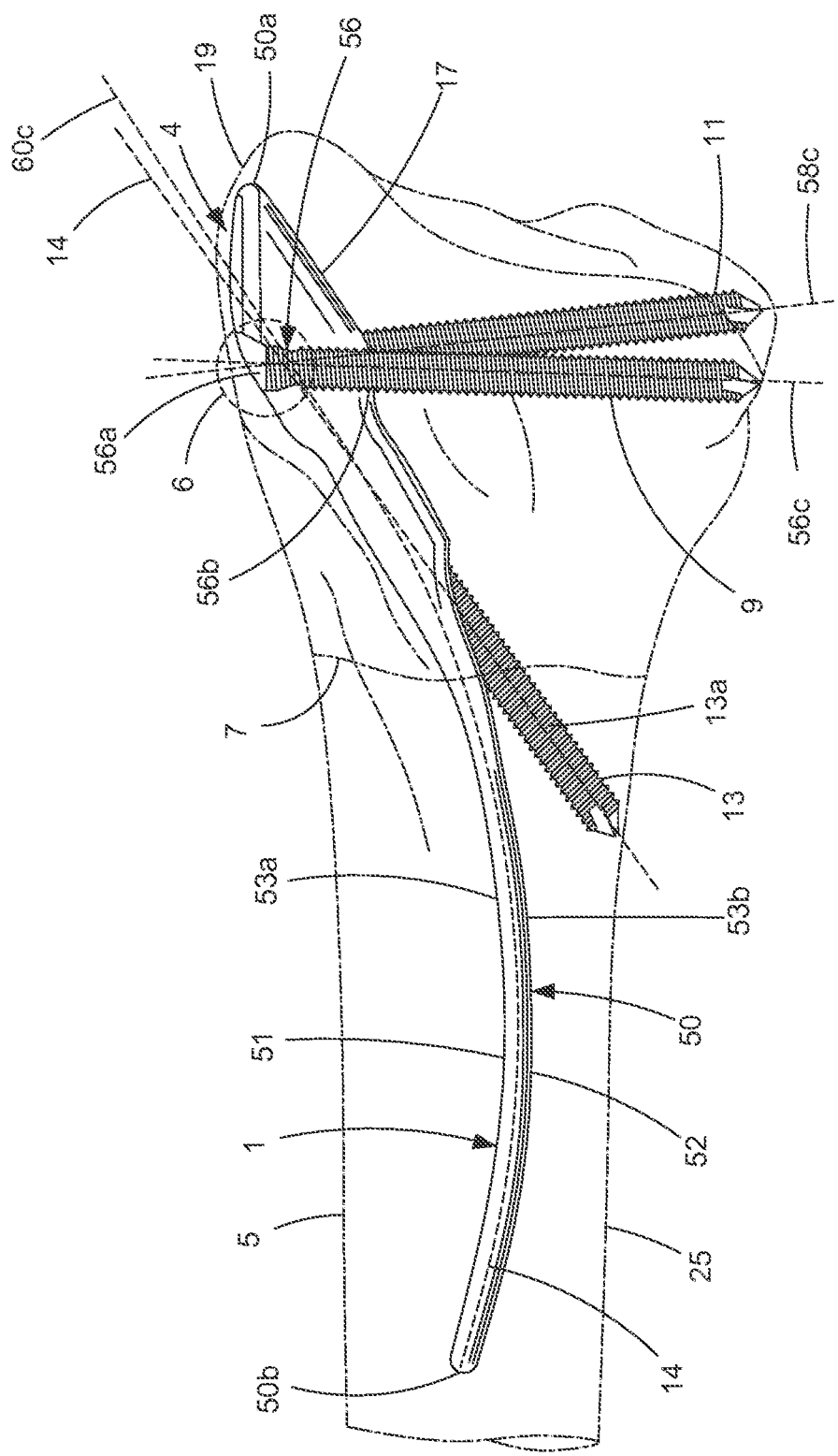
FIG. 1B is a top plan view of an intramedullary fixation assembly similar to FIG. 1A, but constructed in accordance with an alternative embodiment.
Figure 1C:
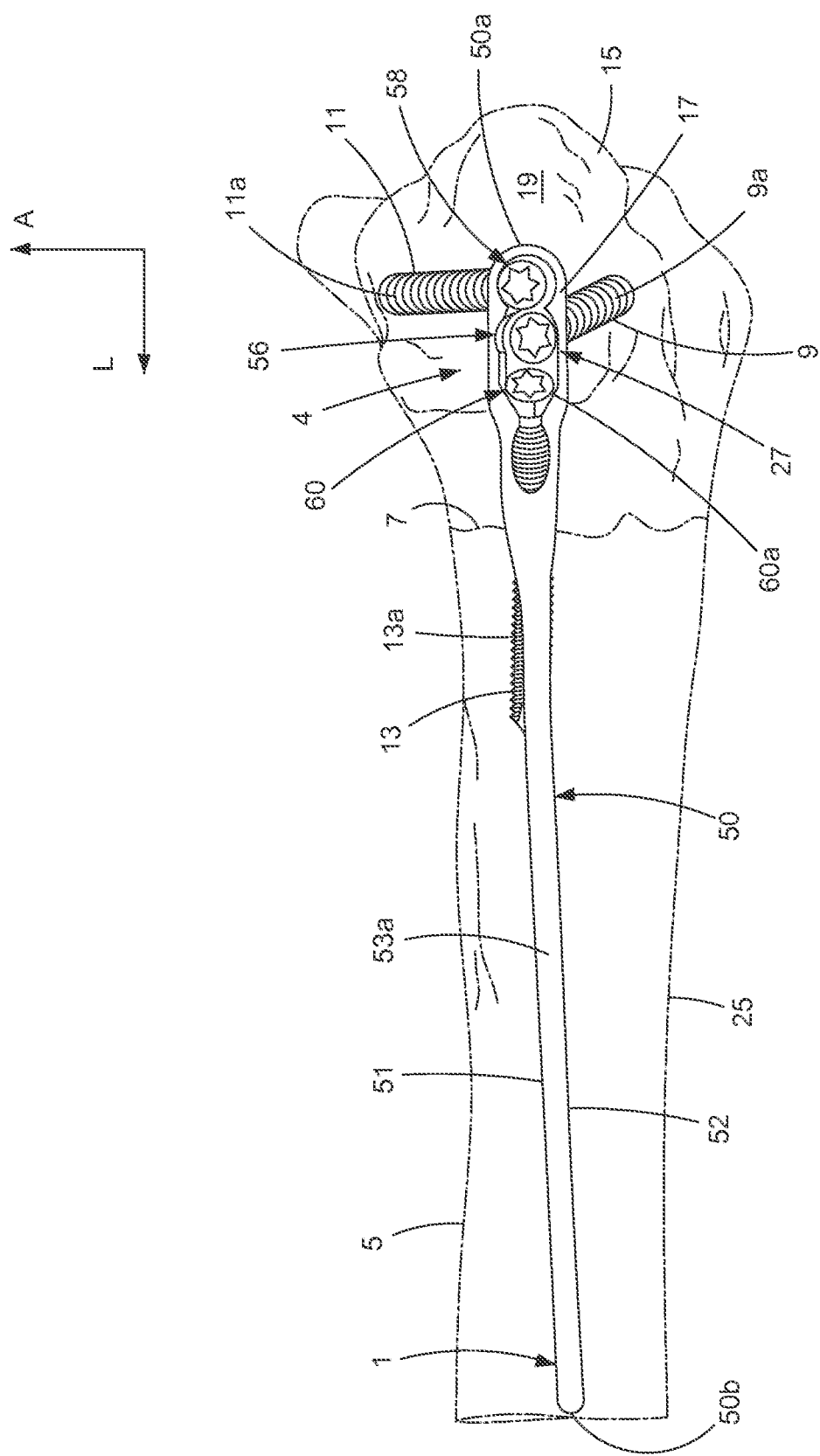
FIG. 1C is a side elevation view of an intramedullary fixation assembly similar to FIGS. 1A-B, but constructed in accordance with an alternative embodiment.

Referring to FIGS. 1A-1C generally, an intramedullary fixation assembly 4, can include a bone fixation device, which can be configured as an intramedullary fixation device 1. The term "intramedullary" is known in the art and denotes that the nail resides at least partly in the medullary canal of a bone. The intramedullary fixation device 1 can be elongate generally along a central axis 14. For instance, the central axis 14, and thus the intramedullary fixation device 1, can be bowed or generally curvilinear in shape along its direction of elongation. The intramedullary fixation device 1 is configured to reside in a medullary canal 3 of a long bone, such as a radius 5 that includes a shaft 25, and a head or articular fragment 15 that extends distally from the shaft 25.

In accordance with the illustrated embodiment, the intramedullary fixation device 1 is sized and configured to extend across a fracture location 7 disposed between the shaft 25 and the articular fragment 15. As used herein, a distal bone fragment can refer to the fragment of a fractured bone in which the fracture line 7 is closest to a joint. For example, the distal fragment is the articular bone fragment 15, and the fracture may be an extra articular fracture. An extra articular fracture is a fracture where the bone has not penetrated the skin, contains only one complete fracture line, and the fracture line does not intersect with part of the joint. Thus, the articular fragment 15 can define a first or distal bone fragment, the shaft 25 can define a second or proximal bone fragment, and the fracture location 7 can separate the first bone fragment from the second bone fragment. As will be appreciated from the description below, the intramedullary fixation device 1 is configured to be inserted through a styloid process 19 of the articular fragment 15 and into the medullary canal 3 so as to extend across the fracture 7, and is further configured to be fixed to both the articular fragment 15 and the shaft 25, thereby stabilizing the articular fragment and the shaft 25 with respect to each other so as to promote bone fixation across the fracture 7. Thus, the intramedullary fixation device 1 can be referred to as a styloid fixation device. It should, of course, be appreciated that a bone fixation device of the type described herein is configured to be used in the temporal bone of the skull, and the ulna, tibia and fibula styloid processes, or any suitable alternative long bone as desired.

The intramedullary fixation device 1 includes a body 50 that defines the head 17 and a shaft 52 that extends proximally from the head 17 so as to define an insertion axis that can be defined by the central axis 14 of the intramedullary fixation device 1. The body 50 can be curved within a plane defined by a longitudinal direction L and a transverse direction T that is oriented substantially perpendicular to the longitudinal direction L. The head 17 can define a free end that defines a first or distal outermost end 50a of the body 50, and the shaft 52 can define a free end that defines a second or proximal outermost end 50b of the body 50 opposite the first outermost end 50a and spaced from the first outermost end 50a along the central axis 14. The first and second ends 50a and 50b can be spaced apart a greater distance along the longitudinal direction L than along the transverse direction T. Thus, the central axis 14 can extend along both the longitudinal direction L and the transverse direction T. Accordingly, the body 50 can define an upper surface 53a, at least a portion of which can be concave in a plane substantially defined by the longitudinal L and transverse T directions, and a lower surface 53b opposite the upper surface 53a along the transverse direction T, at least a portion of which can be convex in the plane substantially defined by the longitudinal L and transverse T directions. The body 50 further extends along a lateral direction A that is substantially perpendicular to the longitudinal direction L and the transverse direction T.

The head 17 can be shaped and dimensioned to reside within the bone structure, such as the styloid process 19 of the radius 5, when the intramedullary fixation device 1 is disposed within the medullary canal 3. In accordance with one embodiment, the shaft 52 may be configured to be elastically deformable to conform to the shape of the medullary canal 3 during implantation. Thus the shaft 52 can be flexible and bowed, which may improve the anchoring of the intramedullary fixation device 1 in the medullary canal 3. The shaft 52 of the intramedullary fixation device 1 can define a longitudinal first fixation element configured to pass across the fracture 7 between the first and second bone fragments. The shaft 52 can be substantially smooth and devoid of threads in accordance with one embodiment, such that the intramedullary fixation device 1 is an intramedullary nail 51 (see FIGS. 1A-C), or can be threaded as desired such that the intramedullary fixation device 1 is an intramedullary screw 29 (see FIGS. 2-3B). Of course, it should be appreciated that any of the intramedullary fixation devices 1 described herein can be constructed as a nail or a screw unless otherwise indicated.

The intramedullary fixation assembly 4 can further include at least one, such as a plurality, of second bone fixation elements, such as screws, that are configured to anchor the intramedullary fixation device 1 to the radius 5, and in particular to the articular fragment 15. For instance, the intramedullary fixation assembly can include a first bone fixation element or screw 9, a second bone fixation element or screw 11, and a third bone fixation element or screw 13. The intramedullary fixation device 1 defines a head 17 that is configured to receive respective heads of the first, second, and third screws 9, 11 and 13, respectively, in the articular fragment 15. The head 17 can be configured to accommodate the screws 9, 11, 13, such that a select one of the screws, for instance the third screw 13, may be configured to pass from the articular fragment 15 to the shaft 25 so as to fix the shaft 25 to the articular fragment 15.

It should be appreciated that the second bone fixation elements can be configured as screws (FIGS. 1A-2) that have a longitudinal core, or staples (FIGS. 3A-B), or the like. The longitudinal cores of the second fixation elements, and also the first fixation element, may be substantially identical in accordance with one embodiment. Having fixation elements with the same core diameter provides the advantage that a reduced number of instruments are able to implant the intramedullary fixation assembly 4 (as compared to an assembly comprising elements with differing diameters), thereby reducing the complexity and costs of the implantation procedure. As used herein, the "core" of a screw can refer to the longitudinal shaft of the screw upon which the thread resides.

The intramedullary fixation device 1 can define at least one channel that is configured to receive a corresponding at least one of the fixation elements that can be configured as screws 9, 11, and 13. In accordance with the illustrated embodiment, the intramedullary fixation device 1, for instance the head 17, can include at least one, such as a plurality, of insertion channels that extends through the body 50, each configured to receive a respective one of the bone fixation elements. For instance, the intramedullary fixation device 1 can define a first insertion channel 56 that extends through the body 50 and is configured to receive the first screw 9, a second insertion channel 58 that is configured to receive the second screw 11, and a third insertion channel 60 that is configured to receive the third screw 13. Each of the insertion channels 56, 58, and 60, respectively, can define an insertion point 56a, 58a, and 60a, respectively, an exit point 56b, 58b, and 60b, respectively, and a channel axis 56c, 58c, and 60c, respectively, that passes through the respective insertion point and the exit point. The screws 9-13 are configured to be inserted into the respective channels 56-60 through the respective insertion point 56a-60a, along the channel axis 56c-60c, and exit through the respective exit point 56b-60b. The head 17 can define an insertion area 27 in which the insertion points 56a-60a, respectively, are located.

As will be described in more detail below with reference to FIGS. 5A-J, the insertion area 27 may be dimensioned and positioned to remain accessible through a single hole in a bone through which the intramedullary nail has been inserted. For instance, the single hole can extend through the styloid process of the radius 5. Thus, the insertion points 56a-60a of all of the insertion channels 56-60 may be located in the insertion area 27. Further, intramedullary fixation device 1 may be completely inserted and fixed in position through a single hole in a bone that can extend, for instance, through the styloid process. Fixation of the intramedullary fixation device 1 is possible with only a single skin incision and through the making of a single bone hole. Additional locking of the second outermost end 50b of the intramedullary fixation device 1 opposed to the insertion area 27 is unnecessary.

The first and second insertion channels 56 and 58 are configured to receive the first and second screws 9 and 11, respectively, and the third channel 60 is configured to receive the third screw 13. In accordance with the illustrated embodiment, the third insertion point 60a extends through the first end 50a of the body 50 substantially coextensive with the central axis 14. Thus, the first and second insertion points 56a and 58a are spaced from the second end 50b a distance that is less than the distance that the insertion point 60a is spaced from the second end 50b.

One of the channels, such as the third channel 60, may be a coextensive channel, such that the third channel axis 60c may be a coaxial channel axis. At least a portion of the coaxial channel axis 60c may be substantially coaxial with the insertion axis, and thus the central axis 14. The insertion channel 60c can extend through the body 50 of the intramedullary fixation device 1 from its insertion point 60a to its exit point 60b, the exit point being 60b located in the shaft 52. The central axis 14 may curve away from the coaxial channel axis 60c in the vicinity of the exit point 60b in a direction from the exit point 60b to the 50b end of the shaft 52. Thus, it can be said that at least a portion of the corresponding third channel axis 60c can be at least partially coaxial, and thus extend longitudinally through (for instance coaxial with, tangential to or intersecting two points of) the central axis 14 of the intramedullary fixation device 1. The third exit point 60b is disposed on an opposite side of the fracture line 7 with respect to the third insertion point 60a. Thus, when the third screw 13 is inserted into the channel 60, a portion of the third screw 13 can cross the fracture line 7. Accordingly, two of the screws 9-13, such as the first and second screws 9 and 11, respectively, are configured to be entirely located in the articular fragment 15, and at least a portion, for instance a tail, of the third screw 13 is configured to extend longitudinally through the intramedullary fixation device 1, and pass from the articular fragment 15 to the shaft 25 across the fracture 7.

At least one, and up to all of, the channels 56-60 can define holes in the head 17 of the intramedullary fixation device 1 that are threaded so as to receive threaded heads of the respective screws 9-13, thereby increasing the stability of the intramedullary fixation device 1. Thus, it can be said that at least one of the plurality of insertion channels, such as the third insertion channel 60, may define a seating area configured to lockingly hold a portion of the respective screws 13 therein. The seating area may be located adjacent the respective insertion point 60a of the at least one of the plurality of insertion channels 60, said at least one of the insertion channels 60 has its exit point 60b located in the shaft 52. Each one of the plurality of insertion channels 56-60 may have a seating area configured to locking hold a portion of the respective fixation element therein 9-13, each seating area located adjacent respective insertion points 56a-60a. Further, the channels 56-60 can be configured according to the type of fixation element they are to receive. The fixation elements may be, but are not limited to, one of a locking screw, such as a fixed angle locking screw or a variable angle locking screw, or a staple.

The central axis 14 of the intramedullary fixation device 1 and at least two, and up to all, of the plurality of channel axes 56c-60c may diverge with respect to each other away from the insertion area 27. For instance, the central axis 14 and at least one up to all of the plurality of channel axes 56c-60c, and thus the respective screws 9-13 that are inserted through the channels 56-60, pyramidally may diverge with respect to each from the insertion area 27. In accordance with the illustrated embodiment, the first and second channels 56 and 58 diverge from each other with respect to the central axis 14 along their respective channel axes 56c and 58c, in a direction from the respective insertion points 56a and 58a to the respective exit points 56b and 58b. Further, the third channel 60 diverges from least one such as both of the first and second channels 56 and 58 with respect to a lateral axis, along their respective channel axes 56c-60c, in a direction from the respective insertion points to the respective exit points. In one embodiment, as shown, for example in FIGS. 1A-C, at least one of channel axes 56c and 58c, and preferably both, diverge from a vertical plane defined by the transverse direction T and the central axis 14 at the head 17 by an angle of at least 5°, preferably at least 10°, and more preferably at least 15°, and it is preferred that the two channels 56c and 58c diverge in opposite directions, one medially and one laterally. This angle is advantageously less than 45°, preferably less than 35°, and more preferably less than 30° for each channel 56c and 58c; the angle is thus advantageously between 5° and 35°; more preferably between 5° and 30°. The channel axis 60c can diverge from a vertical plane defined by the lateral direction A and the channel axis of one of the insertion channels 56c or 58c by an angle of at least 20°, preferably at least 25°, and more preferably at least 35, and is advantageously less than 55°, preferably less than 50°; the angle is thus advantageously between 20° and 55°, more preferably between 25° and 50°.

The screws 9-13 are thus mounted to the head 17 of the intramedullary fixation device 1 so as to form a pyramidal engagement with the radius 5. The pyramidal engagement of the intramedullary fixation device and screws 9-13 with the radius 5 prevents rotation and separation of the articular fragment 15 and the shaft 25, with the exception of micro-movements. For instance, the intramedullary fixation assembly 4, including the intramedullary fixation device 1 and the screws 9-11, may restrict motion in up to six dimensions and have the effect of ensuring that the bone fracture 7 is stably reduced and thereby supporting healing of the radius 5. Thus, the combination of the intramedullary fixation device 1 and the three insertion channels 56-60 and corresponding screws 9-13 is configured to restrict motion of the articular fragment 15 relative to the shaft 25 in six dimensions. It should therefore be appreciated that a stable fixation of the radius 5 is achieved with the requirement of only one skin incision and one bone hole to implant the intramedullary fixation device 1. As a result, a stable fixation of the radius 5 can be achieved, while minimal instrumentation can insert the intramedullary fixation device 1 and minimal trauma is caused to the patient as few incisions in the skin and bone holes are created.

As described above, the screws 9, 11 and 13 can have cores 9a, 11a and 13a of equal diameter thereby requiring only one instrument to insert each distal screw. The screws 9, 11 and 13 form a pyramidal engagement with bone 5, thereby providing a stable fixation of the two bone fragments separated by fracture line 7. The third screw 13 passes across fracture line 7 in order to increase the stability of the engagement. As can be seen clearly in FIG. 1C, the head 17 of the intramedullary fixation device 1 can be configured to receive the first, second, and third screws 9, 11 and 13 in a manner so as to produce the desired pyramidal engagement. The intramedullary fixation device 1 and screws 9, 11 and 13 can be inserted through the styloid process 19 of the radius 5. Advantageously, an entirety of the intramedullary fixation device 1 can be inserted through a single bone hole, advantageously using an insertion device 30 (see FIG. 5) for inserting an intramedullary fixation assembly according to the one embodiment.

In accordance with the embodiments illustrated in FIGS. 1A-C, the plurality of insertion channels 56-60 may include, and can be limited to, three insertion channels. When implanted, two of the central axis 14 or the channel axes of the three insertion channels may extend in a direction from the articular fragment 15 to the shaft 25 that are separated by the fracture 7, and the other two of the central axis 14 and the channel axes of the three insertion channels may extend within the articular fragment 15.

As illustrated in FIGS. 1A-C, a substantial entirety of the first and second insertion channels 56 and 58 are spaced from each other along the lateral direction A. For instance, the first and second insertion points 56a and 58a can be at least partially aligned with each other along the lateral direction A. Similarly, the first and second exit points 56b and 58b can be at least partially aligned with each other along the lateral direction A. Thus, at least a portion of the first and second channel axes 56c and 58c can be at least partially aligned with each other along the lateral direction A. The first and second insertion channels 56 and 58 can diverge away from each other with respect to the central axis 14 along their respective channel axes 56b and 58b along respective directions from the insertion points 56a and 58a to their respective exit points 56c and 58c.

At least a portion, for instance the third insertion point 60a, up to an entirety of the third insertion channel 60 can be disposed between the first and second insertion channels 56 and 58 with respect to the lateral direction A. The third insertion point 60a can further be displaced from the first and second insertion points 56a and 58a proximally along the longitudinal direction L. For instance, the insertion point 60a can be spaced from the second end 50b a distance that is less than the distance that the insertion points 56a and 58a are spaced from the second end 50b. Further, the insertion point 60a, along with the insertion points 56a and 58a, extends through the concave upper surface 53a of the body 50, for instance at the head 17. The first and second screws 9 and 11 are thus configured to extend through the respective first and second channels 56 and 58 and anchor to the articulation fragment 15, and the third screw 13 is configured to extend through the third channel 60 and anchor to the shaft 52. It should thus be appreciated that the intramedullary fixation device 1 defines a region between the third insertion point 60a and the third exit point 60b that is configured to extend across the fracture 7. The third insertion point 60a can lie on the first end 50a, which can extend in a plane that is substantially defined by the transverse T and lateral A directions. As illustrated in FIG. 1B, the first end 50a can extend in a plane that is substantially defined by the longitudinal L and lateral A directions.

In accordance with the embodiment illustrated in FIG. 1C, at least a portion up to all of the first and second insertion channels 56 and 58, including the respective first and second insertion points 56a and 58a, the first and second exit points 56b and 58b, and the first and second channel axes 56c and 59c, can be further spaced from each other along the longitudinal direction L as desired. Furthermore, at least a portion up to all of the first and second insertion channels 56 and 58, including the respective first and second insertion points 56a and 58a, the first and second exit points 56b and 58b, and the first and second channel axes 56c and 59c, can be aligned with each other along the longitudinal direction L as desired. In accordance with the illustrated embodiment, the third channel 60 can be disposed distal to the first and second channels 56 and 58. For instance, the third insertion point 60a, the third channel axis 60b, and the third exit point 60c can be disposed distal to the respective first and second insertion points 56a and 58a, the first and second channel axes 56ba and 58b, and the first and second exit points 56c and 58c, respectively. Further, in accordance with the illustrated embodiment, the first channel 56 can be disposed between the second and third channels 58 and 60 with respect to the longitudinal direction L. For instance, the first insertion point 56a, the first channel axis 56b, and the first exit point 56c can be disposed between the respective second and third insertion points 58a and 60a, the second and third channel axes 58ba and 60b, and the second and third exit points 58c and 60c, respectively. As described above, the channels 56-60, and thus the respective retained screws 9-13, can diverge from each other so as to define a pyramidal construct.

Figure 2:
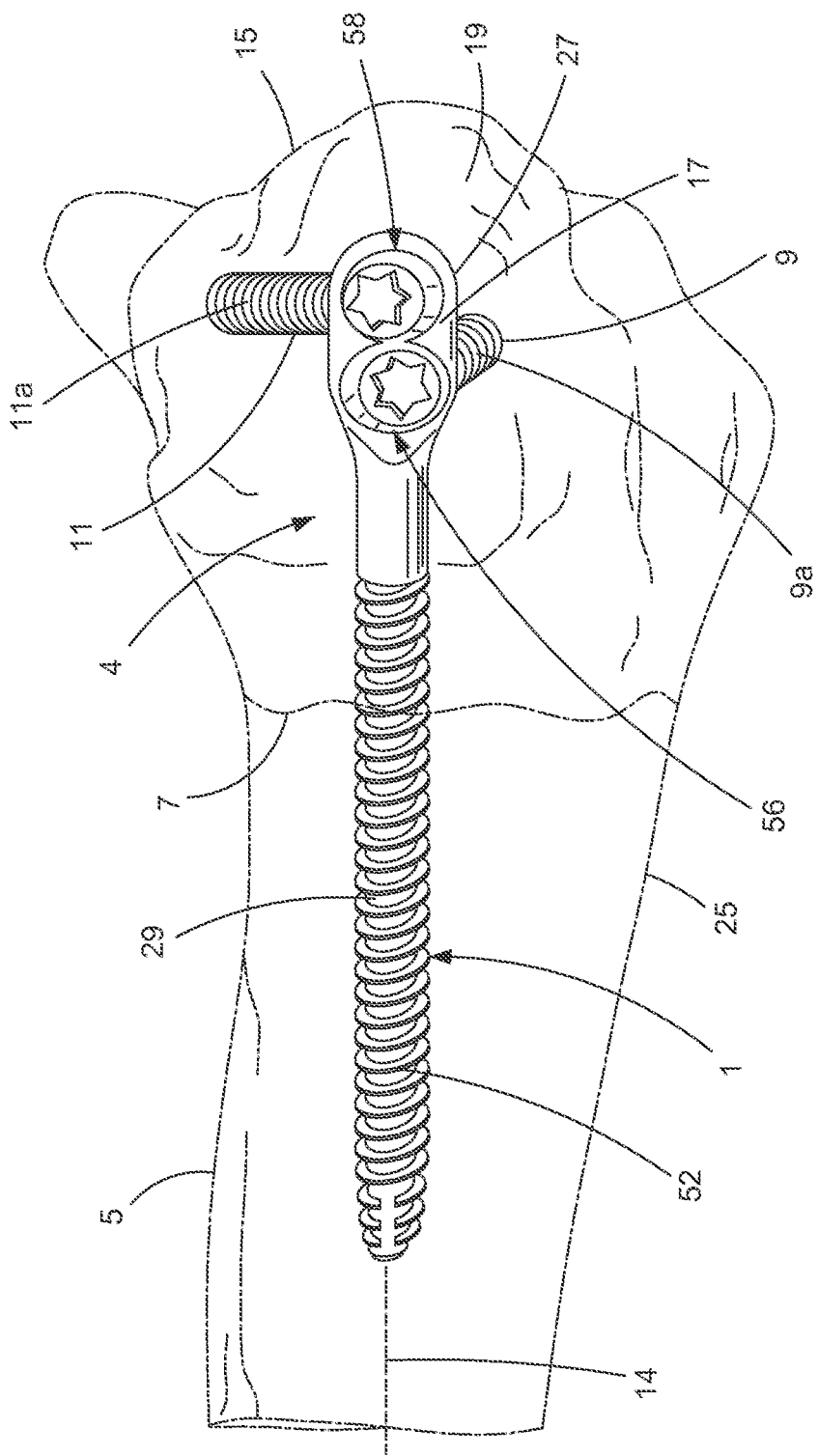
FIG. 2 is a top plan view of an intramedullary fixation assembly in accordance with another embodiment.

Referring now to FIG. 2, the intramedullary fixation device 1 can be configured substantially as described above with respect to FIGS. 1A-C, but wherein the shaft 52 defines externally threads 31 such that the intramedullary fixation device 1 defines an intramedullary screw 29. Accordingly, the shaft 52 can be configured as a bone fixation element that is configured to attach to bone so as to attach the intramedullary fixation device 1 to the radius 5. The shaft 52 can extend substantially linearly from the head 17, such that the central axis 14 is likewise substantially linear. The intramedullary fixation device 1 can define first and second insertion channels 56 and 58, and may be limited to two insertion channels. Alternatively, the intramedullary fixation device 1 illustrated in FIG. 2 can include any number of channels as described in any one of FIGS. 1A-1C. In accordance with the illustrated embodiment, at least a portion up to all of the first and second insertion channels 56 and 58, including the respective first and second insertion points 56a and 58a, the first and second exit points 56b and 58b, and the first and second channel axes 56c and 59c, can be aligned with each other along the longitudinal direction L as desired.

The first and second channels 56 and 58 extend through the insertion area 27 of the head 17, and can diverge from each other with respect to the central axis 14 as described above, and the shaft 52 can diverge from each of the first and second channels 56 and 58 with respect to a lateral axis, as described above. For instance, the insertion paths may be defined by the shaft 52 and the plurality of insertion channels 56 and 58 pyramidally diverging with respect to each other from the insertion area 27. Thus, the shaft 52 and the first and second screws 9 and 11 that are inserted in the first and second channels 56 and 58 are configured to define the pyramidal construct described above. The fixation elements, including the shaft 52, and the first and second screws 9 and 11, may form a pyramidal engagement with the bone, the angle between the elements at the vertex of the pyramid at the insertion area on the head of the intramedullary nail may all be different or equal and may be 109.5°, or 100°, or 90°, or 80°, or 70°, or 60°. There may be a pair of fixation elements, such as screws 9 and 11, in which the angle between them at the vertex of the pyramid is, for example 60° and the third fixation element, for instance the shaft 52, is at an angle of 100° from each of the pair of fixation elements.

When implanted in the radius 5, one of the central axis 14 or one of the channel axes 56c and 58c of the two insertion channels 56 and 58, respectively, may extend in a direction from the articular fragment 15 to the shaft 25 that are separated by the fracture 7, and the other two of the central axis 14 and the channel axes 56c and 58c of the two insertion channels 56 and 58 may extend within the articular fragment 15. For instance, the head 17 can be configured to be disposed in the articular fragment 15, and the threaded shaft 52 is configured to extend from the head 17, across the fracture 7, and into the medullary canal 3 defined by the shaft 25 of the radius 5. The threads 31 can be disposed in at least one or both of the articular fragment 15 and in the shaft 25.

It should thus be appreciated that intramedullary fixation assembly 4 can include a bridging element that is configured to attach the shaft 25 to the articular fragment 15 through insertion of the bridging element in the vicinity of the single bone hole. When the intramedullary fixation device 1 is implanted in the radius 5, at least one of the intramedullary fixation device 1, such as the shaft 52, the first screw 9 and the second screw 11 is a bridging element arranged to span across a bone fracture 7 from the articular fragment 15 to the shaft 25, and at least one of the intramedullary fixation device 1, such as the shaft 52, the first screw 9 and the second screw 11 is arranged to lie within the articular fragment 15. The bridging element may have a multi-faceted outer surface for engaging with the medullary canal 3 of the articular fragment 15 and the shaft 25. When implanted two of the shaft and the first, second and third fixation elements may be bridging elements and the other two of the shaft and the first, second and third fixation elements may lie within the first bone fragment. A fixation element separate from the intramedullary fixation assembly 4 may be additionally inserted from the articular fragment 15 to the shaft 25 so as to lock the articular fragment 15 and the shaft 25 together and restrict motion in six dimensions.

Figure 3A:
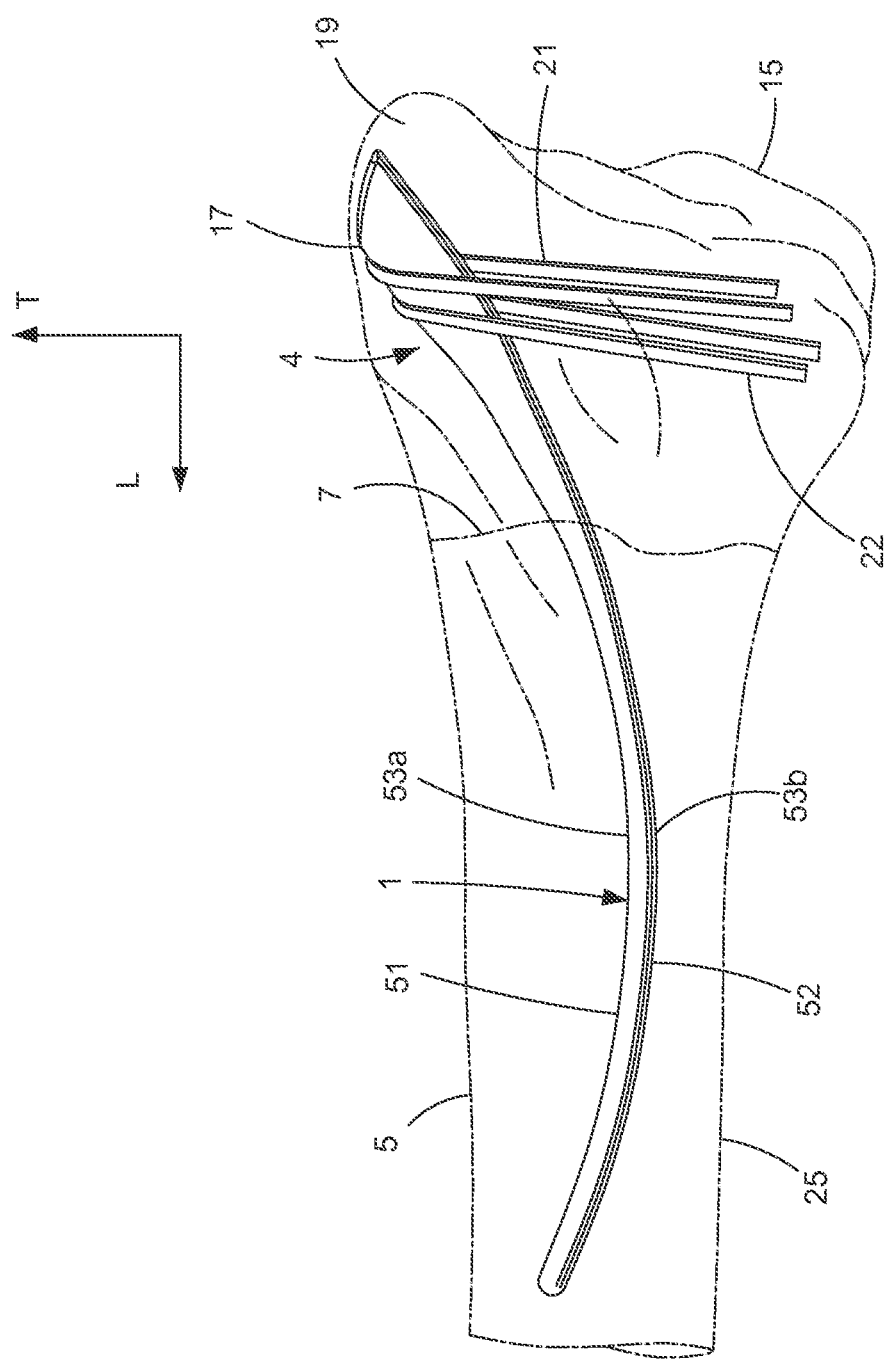
FIG. 3A is a perspective view of an intramedullary fixation assembly in accordance with another embodiment.

Referring now to FIG. 3A, as described above, the second fixation elements of the intramedullary fixation assembly 4 can be configured as staples, such as a first staple 21 and a second staple 22. For instance, each of the first and second staples 21 and 22 can wrap around at least a portion of the body 50 of the intramedullary fixation device 1. In accordance with the illustrated embodiment, each of the first and second staples 21 and 22 can wrap around the head 17 of the intramedullary fixation device 1 so as to define at least a partial revolution about the head 17. For example, each of the first and second staples 21 and 22 can wrap around the upper surface 53a of the head 17, such that opposed free ends of the staples 21 and 22 are configured to anchor in the articular fragment 15, and an intermediate portion that extends between the free ends is wrapped about the head 17. The free ends of each staple can be disposed on laterally opposite sides of the intramedullary fixation device 1, such that the intramedullary fixation device 1 is disposed between the free ends of each of the staples with respect to the lateral direction A. The first staple 21 can be spaced from the second staple 22 along the longitudinal direction L, and the free ends of the staples 21 and 22 can be spaced from the head 17 along at least the transverse direction T, for instance in addition to the lateral direction A as desired. Further, the free ends of the first staple 21 can be offset with respect to the free ends of the second staple 22 along the lateral direction A, or can be aligned with the free ends of the second staple 22 along the lateral direction A as desired. The staples 21 and 22 are configured to form an angular construct which provides a stable fixation of the bone fragments separated by fracture line 7.

Figure 3B:
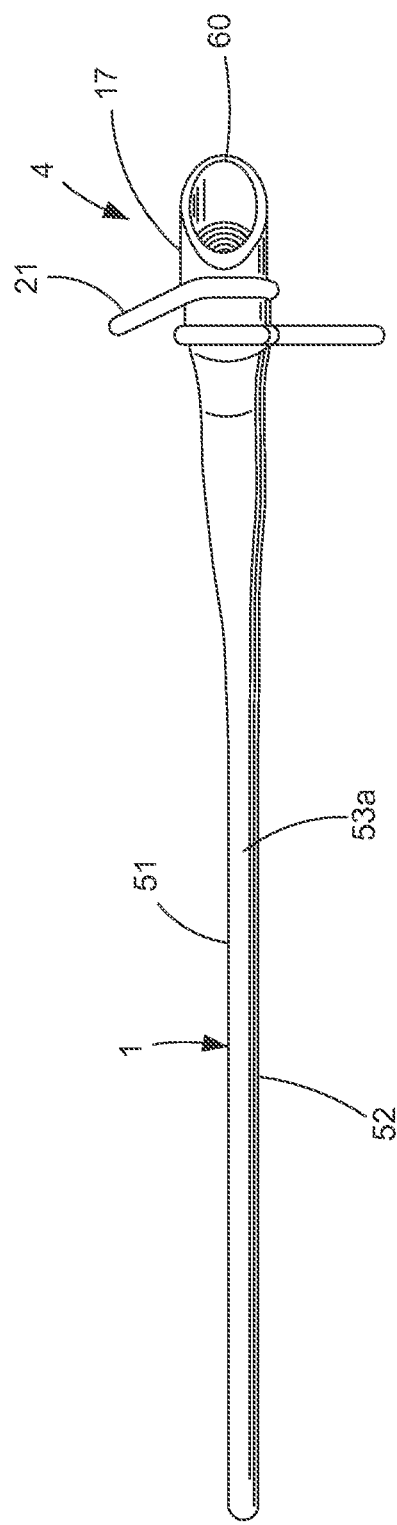
FIG. 3B is a top plan view of an intramedullary fixation assembly similar to the intramedullary fixation assembly illustrated in FIG. 3A, but constructed in accordance with an alternative embodiment.

It should be appreciated that the intramedullary fixation assembly 4 can include any number of staples as desired. For instance, as illustrated in FIG. 3B, the intramedullary fixation assembly 4 can include a single staple 21 that can wrap around at least a portion of the body 50 of the intramedullary fixation device 1. In accordance with the illustrated embodiment, the staple 21 can wrap around the head 17 of the intramedullary fixation device 1 so as to define at a full revolution about the head 17. For example, the staple 21 can wrap around the upper surface 53a of the head 17 and the lower surface 53b of the head 17, such that the opposed free ends the staple 21 are configured to anchor in the articular fragment 15, and an intermediate portion of the staple 21 that extends between the free ends is wrapped about the head. The free ends of the staple 21 can be disposed on laterally opposite sides of the intramedullary fixation device 1, such that the intramedullary fixation device 1 is disposed between the free ends the staple with respect to the lateral direction A. One of the free end so the staple 21 can be spaced from the other of the free ends of the staple 21 along the longitudinal direction L, and the free ends of the 21 can be spaced from the head 17 along at least the transverse direction T, for instance in addition to the lateral direction A as desired. The free ends of the staple 21 are configured to form an angular construct which provides a stable fixation of the bone fragments separated by fracture line 7. Thus, it should be appreciated that the intramedullary fixation assembly 4 can include at least one staple, such as a plurality of staples that can be wrapped about the intramedullary fixation device 1 along at least a partial revolution. The shaft 52 of the intramedullary fixation device 1 illustrated in FIGS. 3A-B can be constructed as described above, and can thus be curved and substantially smooth, or can alternatively be externally threaded, as described above. Furthermore, the head 17 can define the channel 60 that is configured to receive a screw that is configured to extend coaxially from the head 17 across the fracture 7 to the shaft 25 as described above.

Figure 4A:
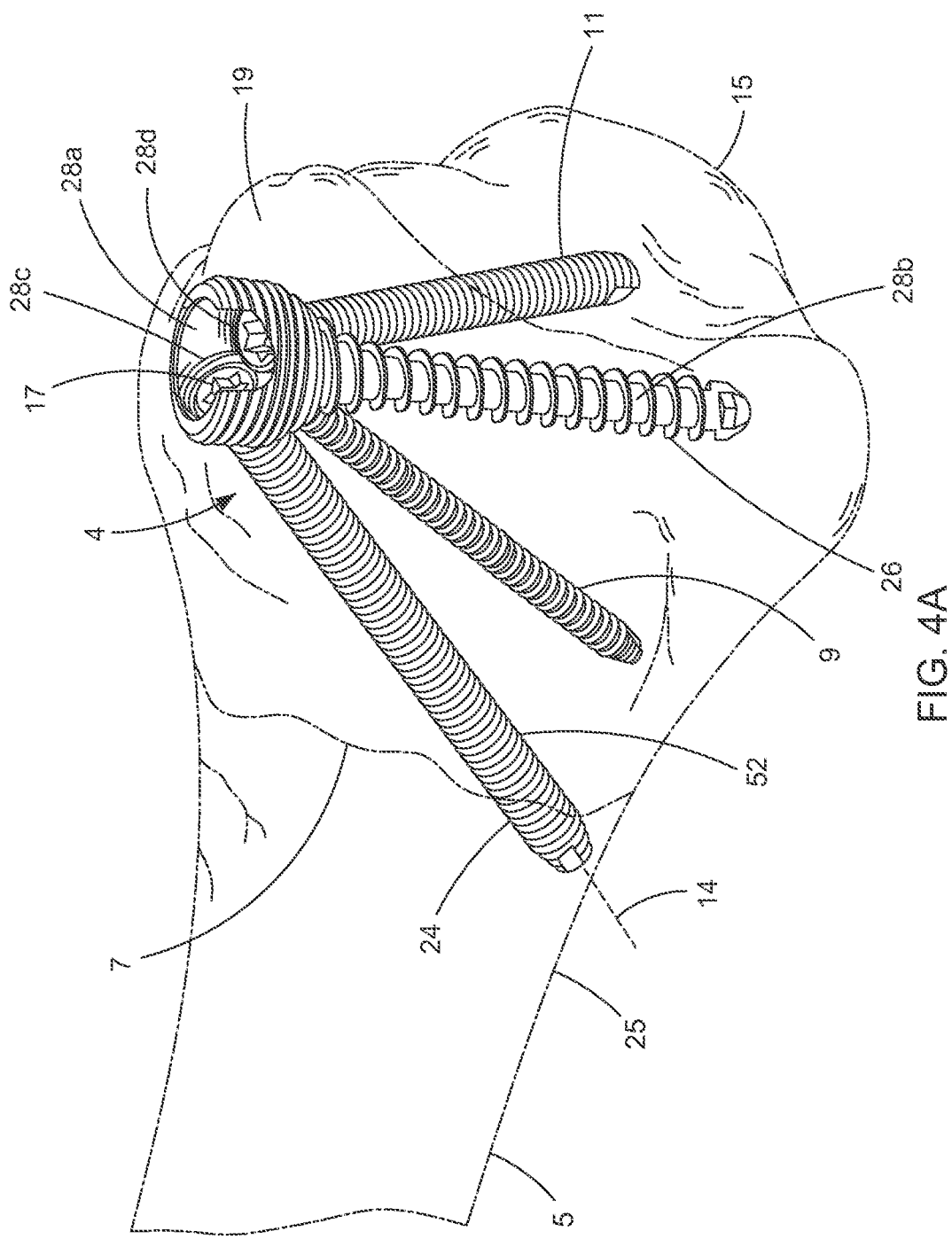
FIG. 4A is a perspective view of an intramedullary fixation assembly in accordance with one embodiment.

Referring now to FIG. 4A, an intramedullary fixation assembly 4 can include an intramedullary fixation device 24, which can be in the form of a threaded screw having a head 17 and a shaft 52 that extends distally from the head 17, that is configured to pass from the articular fragment 15 to the shaft 25 across the fracture 7. The intramedullary fixation assembly 4 can further include a first fixation element 26, which can be a screw that defines a head 28a and a threaded shaft 28b that extends distally from the head 28a along a central axis. The intramedullary fixation device 24, and in particular the shaft 52, is adapted to extend through an aperture 28c that extends through the head 28a of the first fixation element 26 at an angle oblique to the central axis of the threaded shaft 28b so as to be anchored in the shaft 25 of the radius 5. The head 17 of the intramedullary fixation device 24 can define externally threads, and the aperture 28c can define internal threads that mate with the external threads of the head 17 so as to attach the head 17 of the intramedullary fixation device 24 to the head 28a of the first fixation element 26. The first fixation element 26, and in particular the threaded shaft 28b, is configured to anchor the first fixation element 26, and thus the intramedullary device 24, for instance the head 17 of the intramedullary device 24, in the articular fragment 15 of the radius 5.

The intramedullary fixation assembly 4 can include at least one second fixation element, such as second fixation elements configured as screws 9 and 11 that are also received in the head 28a of first fixation element 26. For instance, the first fixation element 26 can include at least one auxiliary aperture 28d that are circumferentially spaced about the head 28a. For instance, the apertures 28c and 28d can be equidistantly spaced from each other or spaced from each other at variable distances. The auxiliary apertures 28d can be configured to receive respective second fixation elements, which can be configured as first and second screws 9 and 11, respectively. In accordance with the illustrated embodiment, the heads of the screws 9 and 11 can be externally threaded, and the auxiliary apertures 28d can be internally threaded so as to mate with the heads of the first and second screws 9 and 11 to thereby attach the first and second screws to the head 28a. The screws 9 and 11 are configured to anchor to the articular fragment 15. The shafts of the screws 9 and 11 are elongate along respective central axes that are angularly offset with respect to each other, the shaft 26b, and the shaft 52. Thus, the screws 9 and 11, the shaft 28b, and the shaft 52 can define a pyramidal anchor in the radius 5. It should be appreciated that at least some up to all of the screws 9 and 11, the shaft 28b, and the shaft 52 can have the same core diameter.

Figure 4B:
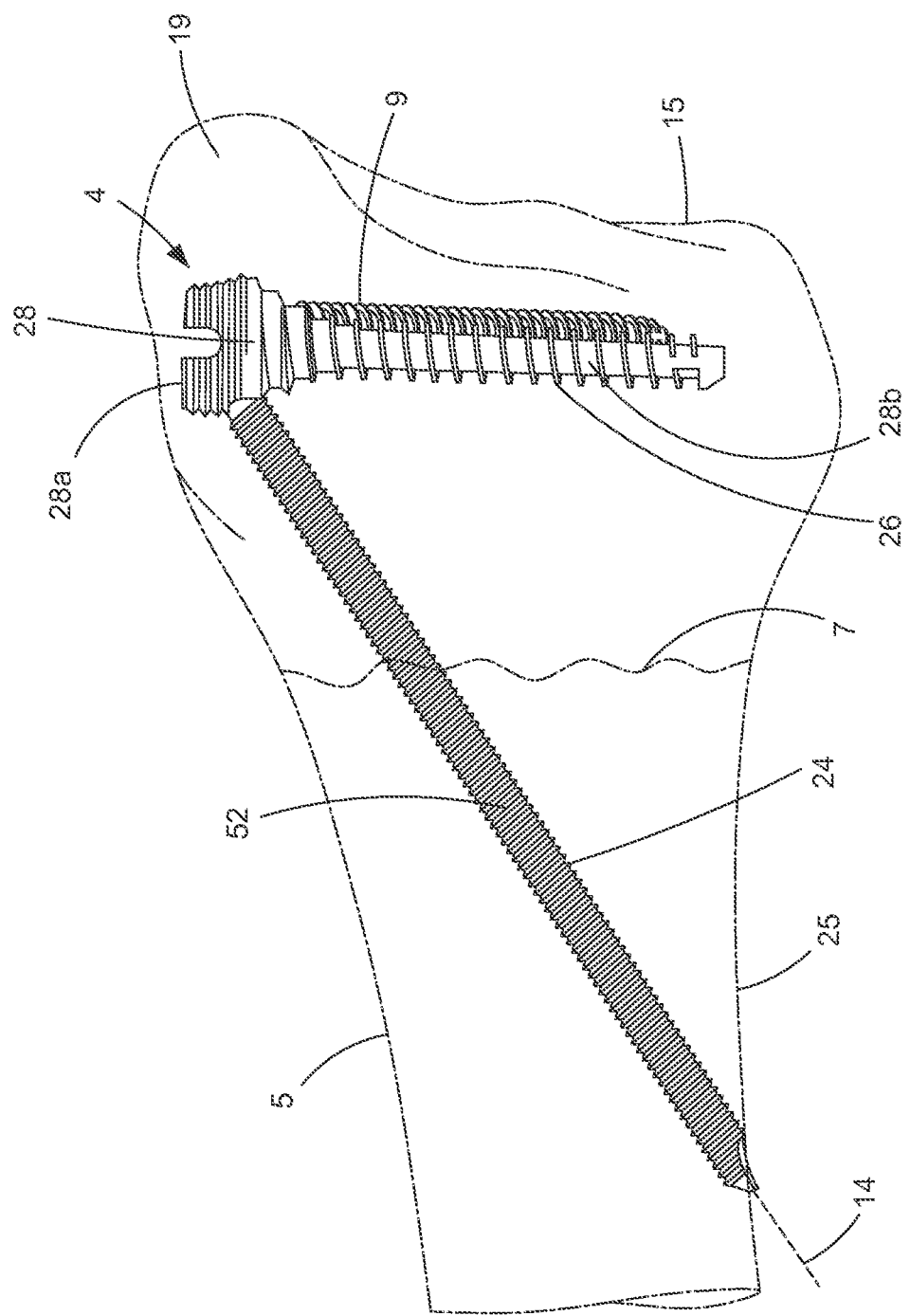
FIG. 4B is a side elevation view of an intramedullary fixation assembly similar to FIG. 4A, but constructed in accordance with another embodiment.

As illustrated in FIG. 4A, the head 28a is configured to receive a pair of screws 9 and 11. As illustrated in FIG. 4B, the intramedullary fixation assembly 4 can include a single screw 9 that is configured to be attached to the head 28a. For instance, the first fixation element 26 can define a single auxiliary aperture 28d that extends through the head 28a and is configured to receive and attach to the head of the screw 9 in the manner described above. The screw 9 is configured to anchor to the articular fragment 15. The shaft of the screw 9 can be angularly offset with respect to the central axis 14 of the intramedullary device 24, such that the shaft of the screw 9, the shaft 28b, and the shaft 52 can define a pyramidal construct of the type described above.

Figure 5A:
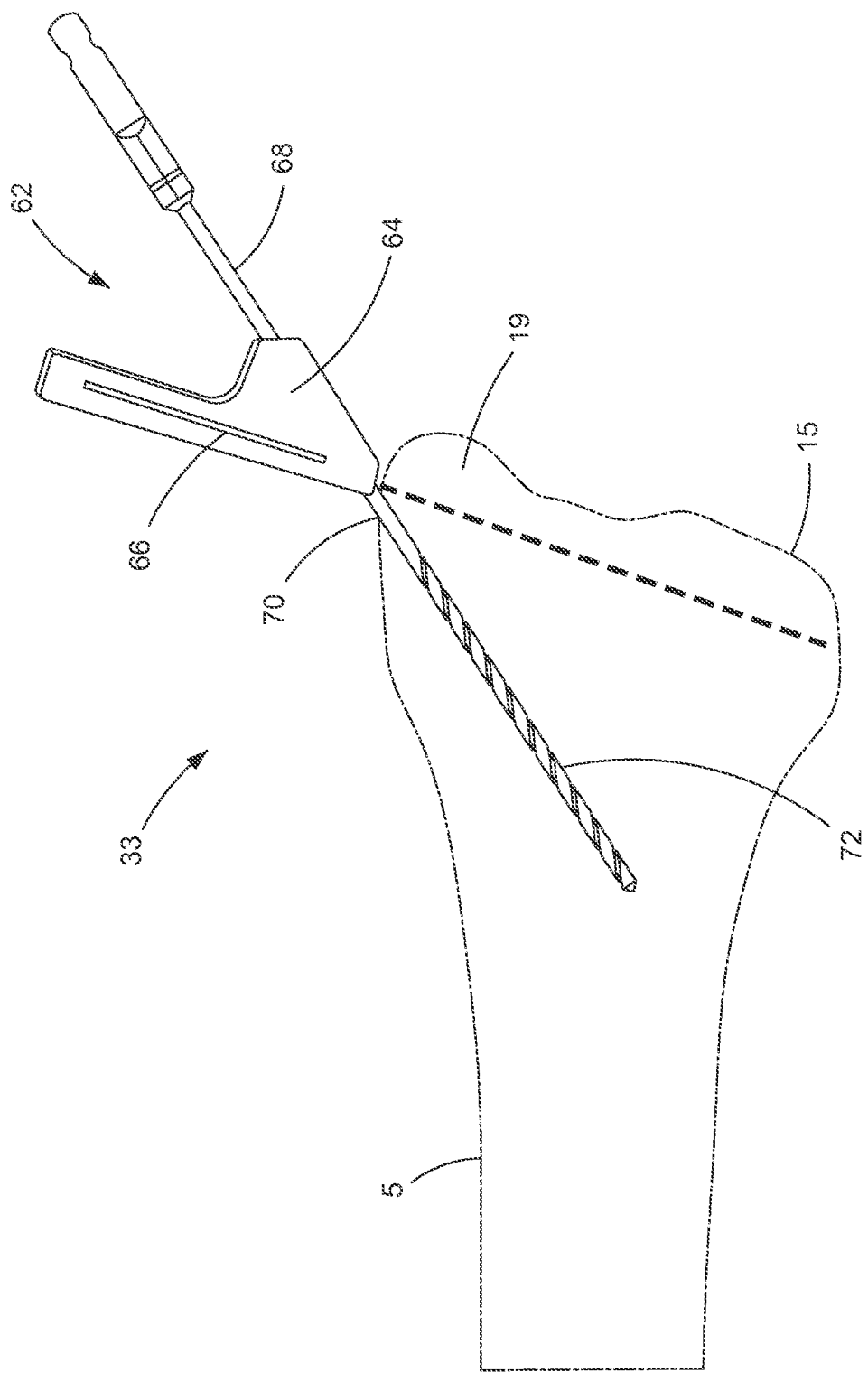
FIGS. 5A-J show an insertion assembly and associated steps inserting and fixing an intramedullary fixation assembly in accordance with one embodiment.

Referring to FIG. 5A, an intramedullary fixation system 33 can include the intramedullary fixation system of the type described above along with insertion instrumentation 62 is configured to insert and fix an intramedullary fixation assembly 4 to the radius 5. The instrumentation 62 can include a drilling guide 64 that can be made from a radiolucent material, for instance polyetheretherketone (PEEK), and a drill 68. The drilling guide 64 can include one or more radio-opaque markings 66 visible on an x-ray. As used herein, radiolucent can refer to a material that allows the passage of x-rays with little attenuation, thereby rendering the material substantially invisible by x-ray imaging. For instance, the one or more markings 66 can include first and second markings that are aligned with respective first and second trajectories along which the respective second and third fixation elements 11 and 13 are to be inserted into the styloid process 19. When the at least one marking 66 is aligned as desired, a drill 68 can be inserted through the drill guide 64 and guided along a desired trajectory so as to create an opening 70 through the styloid process 19, and a channel 72 that extends from the opening 70 across the fracture 7, the channel configured to guide the intramedullary fixation device 1 into the medullary canal 3. The trajectory defined by the at least one marking 66 can be aligned with the opening 70, such that the first and second screws 9 and 11 can be inserted into the respective first and second channels 56 and 58 through the opening 70.

Figure 5B:
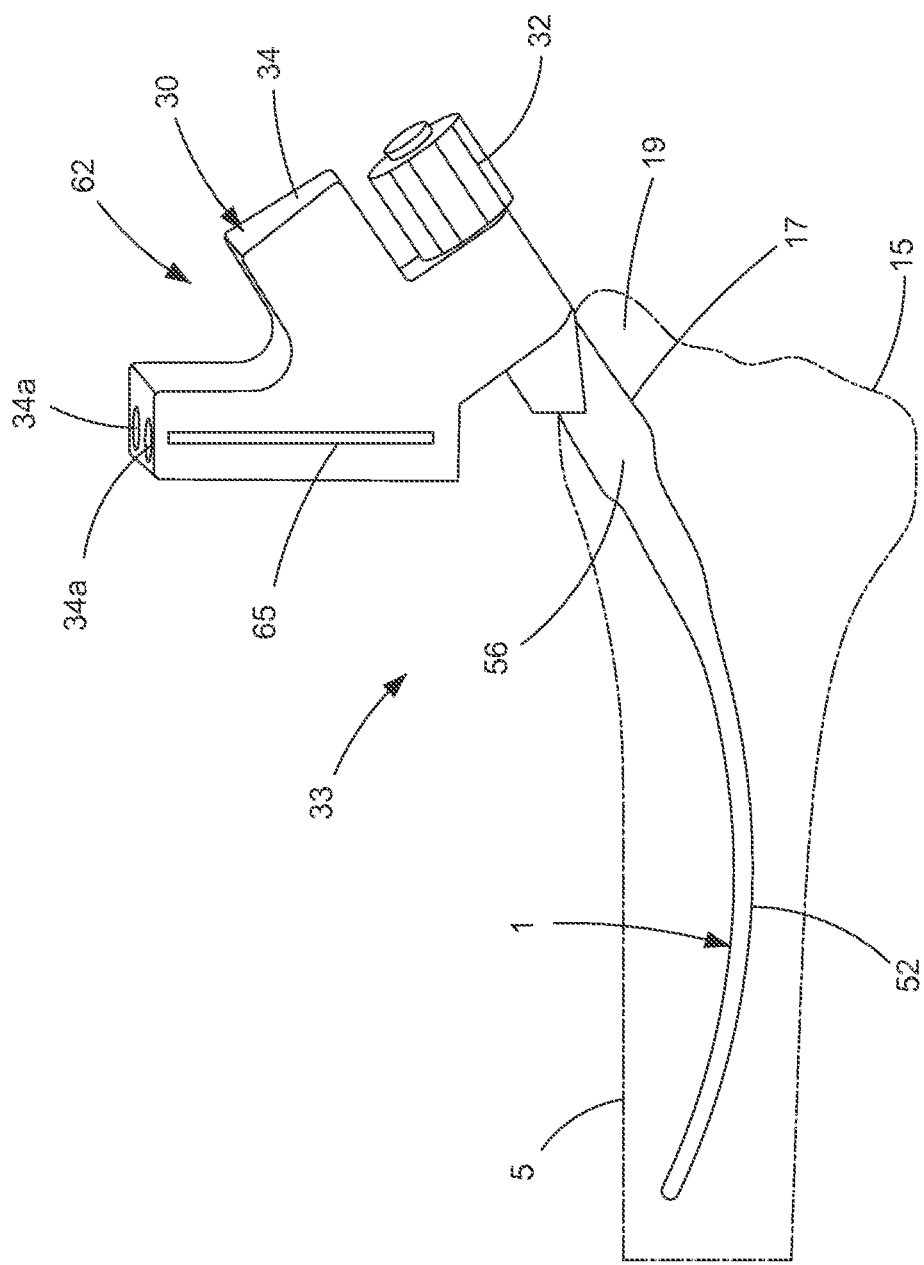

For instance, referring now to FIG. 5B, the insertion instrumentation 62 can further include an insertion device 30 having an aiming arm 34 and a part 32, such as a pusher, that is configured to be coupled to the aiming arm 34 and urge the intramedullary fixation device 1 through the drilled opening 70 and into the channel 72, such that the intramedullary fixation device 1 can be inserted into the medullary canal. The intramedullary fixation device 1 can be constructed as desired, for instance as described and illustrated above. Thus, the aiming arm 34 may be connectable to the intramedullary fixation device 1, and may define a plurality of guide channels 34a therein. Each guide channel 34a may have a guide axis aligned with a respective channel axis of an insertion channel of the intramedullary fixation device 1, the channel axes diverging from an insertion area defined in a head 17 of the intramedullary fixation device 1, as described above.

Figure 5C:
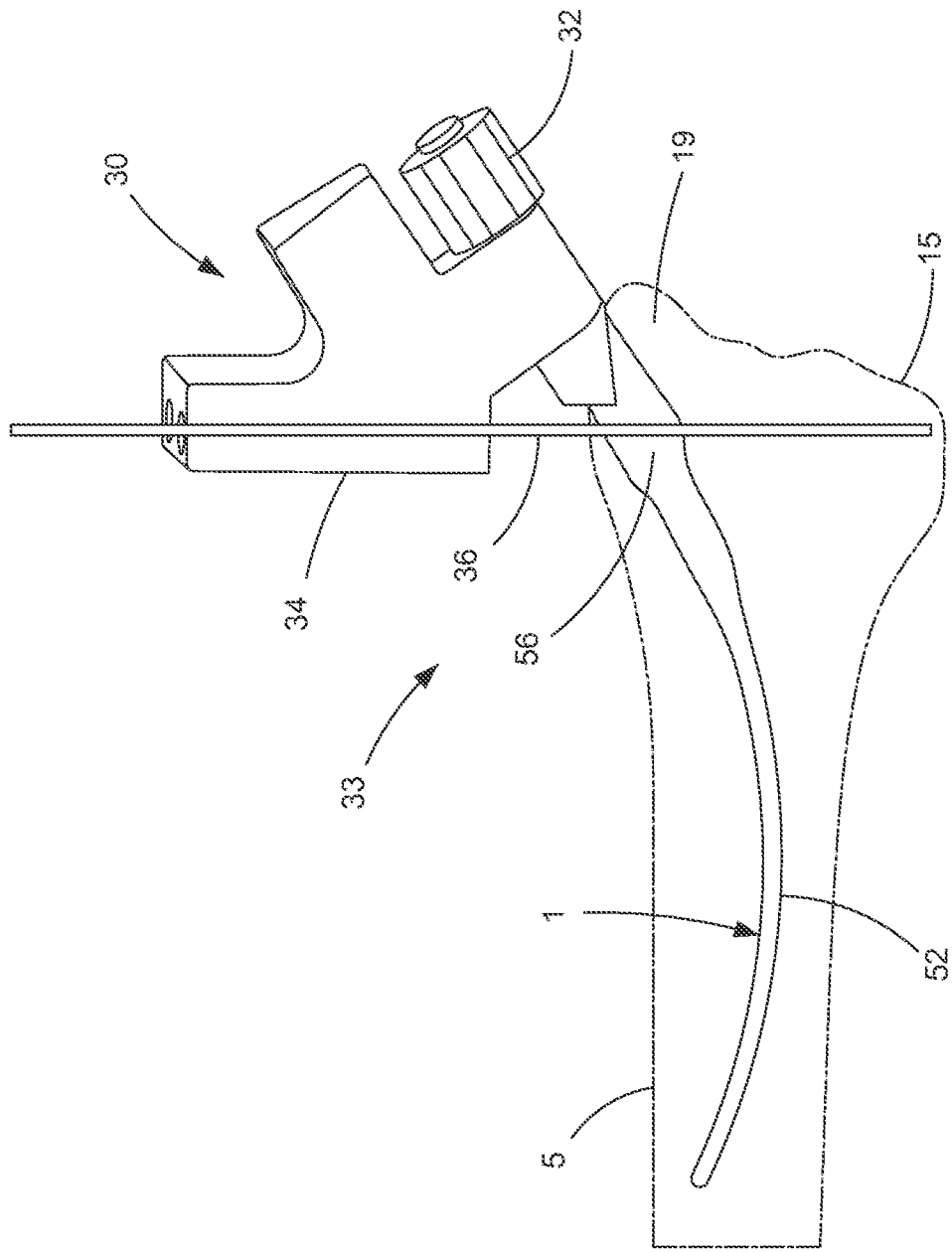

The aiming arm 34 can include, consist of or consist essentially of a radiolucent material. The radiolucent material is polyether ether ketone (PEEK). The aiming arm 34 may have an x-ray visible mark. For instance, the aiming arm 34 can include one or more radio-opaque markers 65 that define the same trajectory or trajectories as previously defined by the one or more radio-opaque markers 66 of the drill guide 64 as described above with respect to FIG. 5A. As illustrated in FIG. 5C, a pair of k-wires 36 can be inserted through aiming arm 34 along the first and second the trajectories as indicated by the radio-opaque markers 65, and thus through the drilled opening 70 and into the styloid process 19. The K-wires are thus inserted through the head 17 of intramedullary fixation device 1, and in particular through the first and second openings 56 and 58 of the type described above.

Figure 5D:
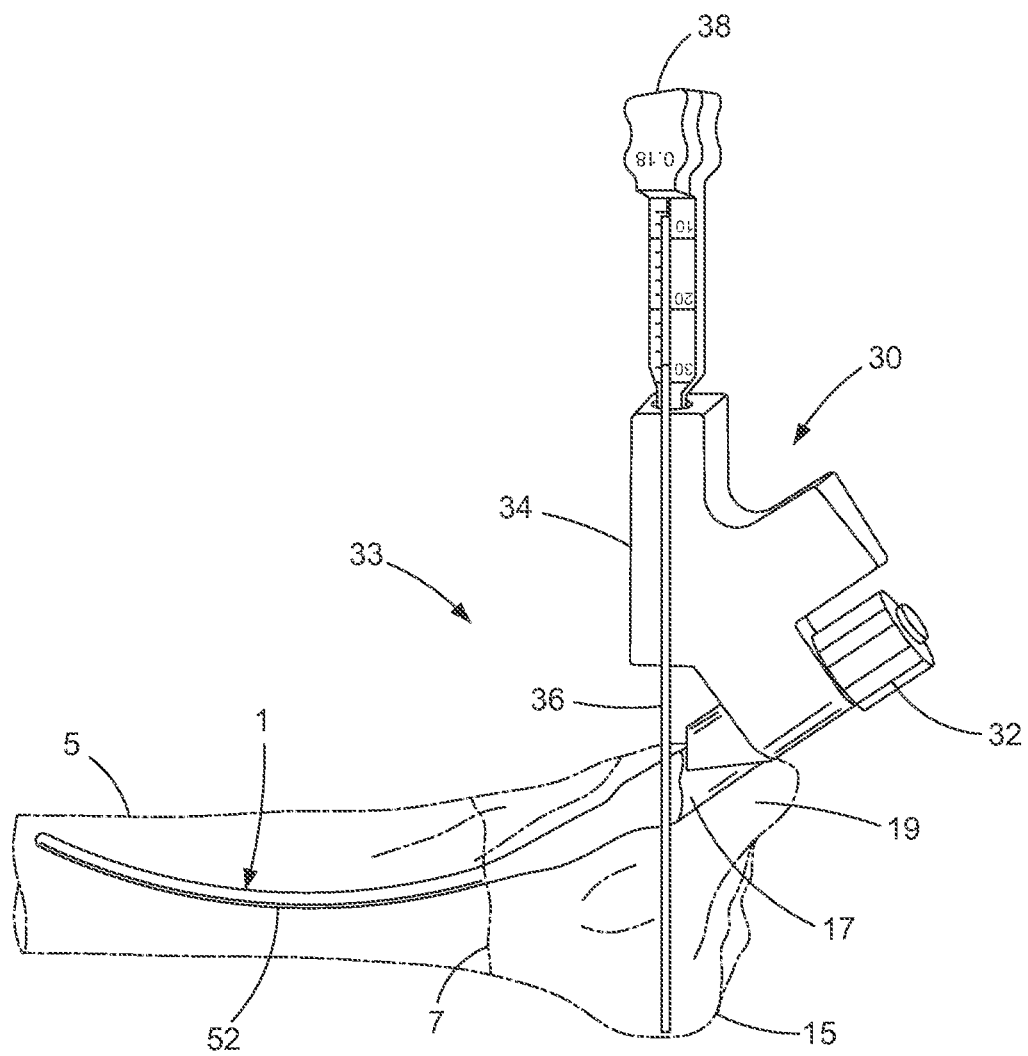
Figure 5E:
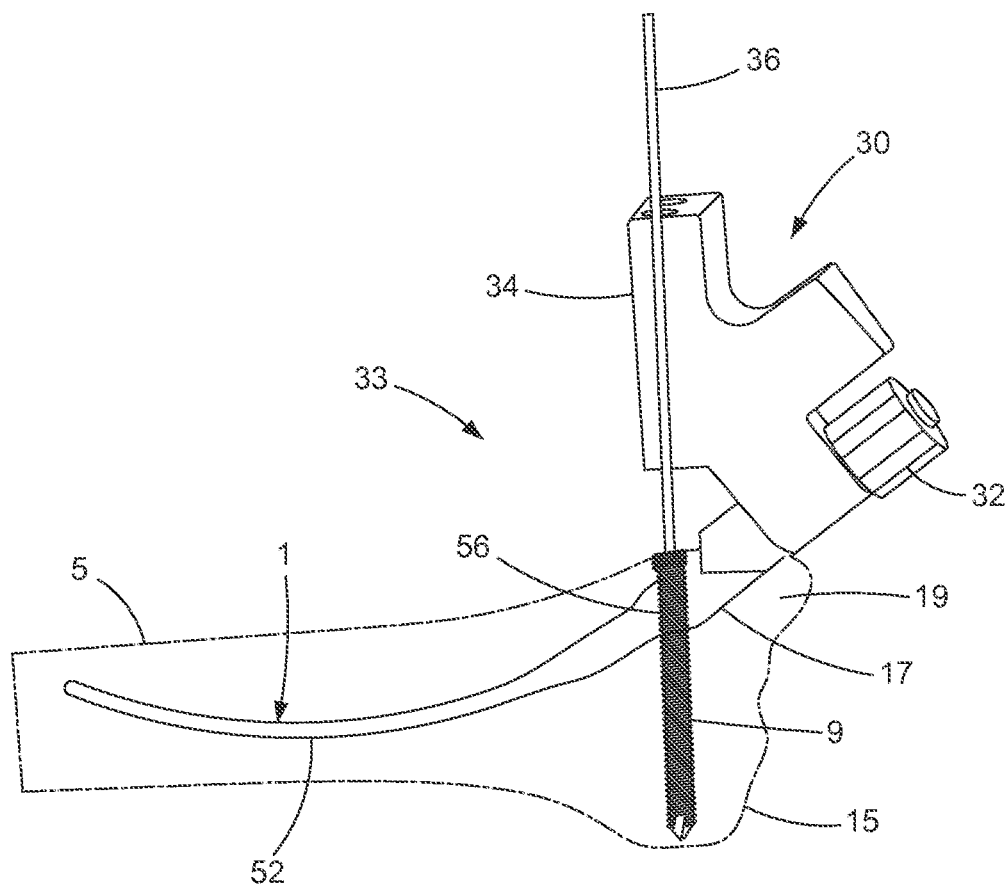
Figure 5F:
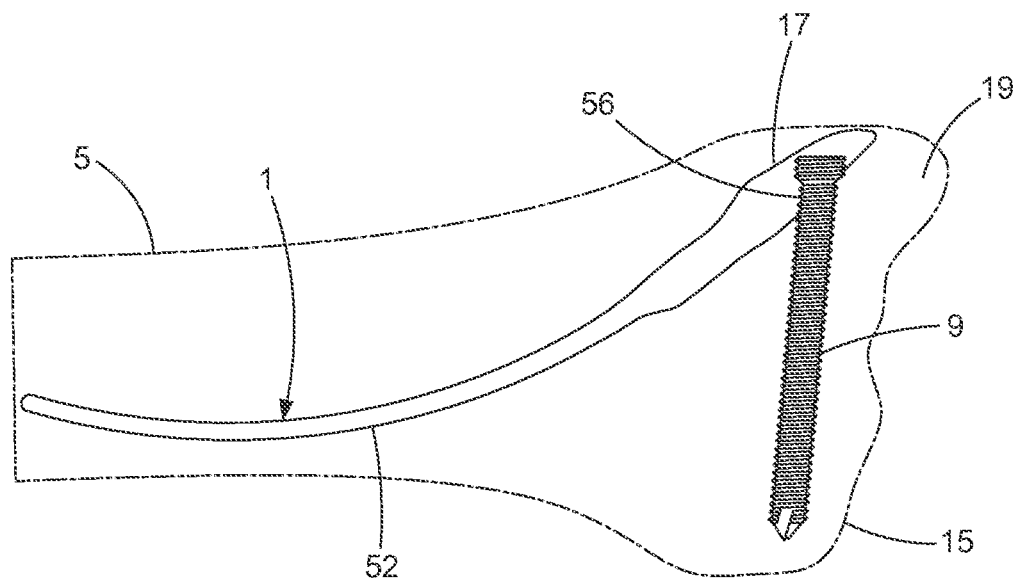
Figure 5G:
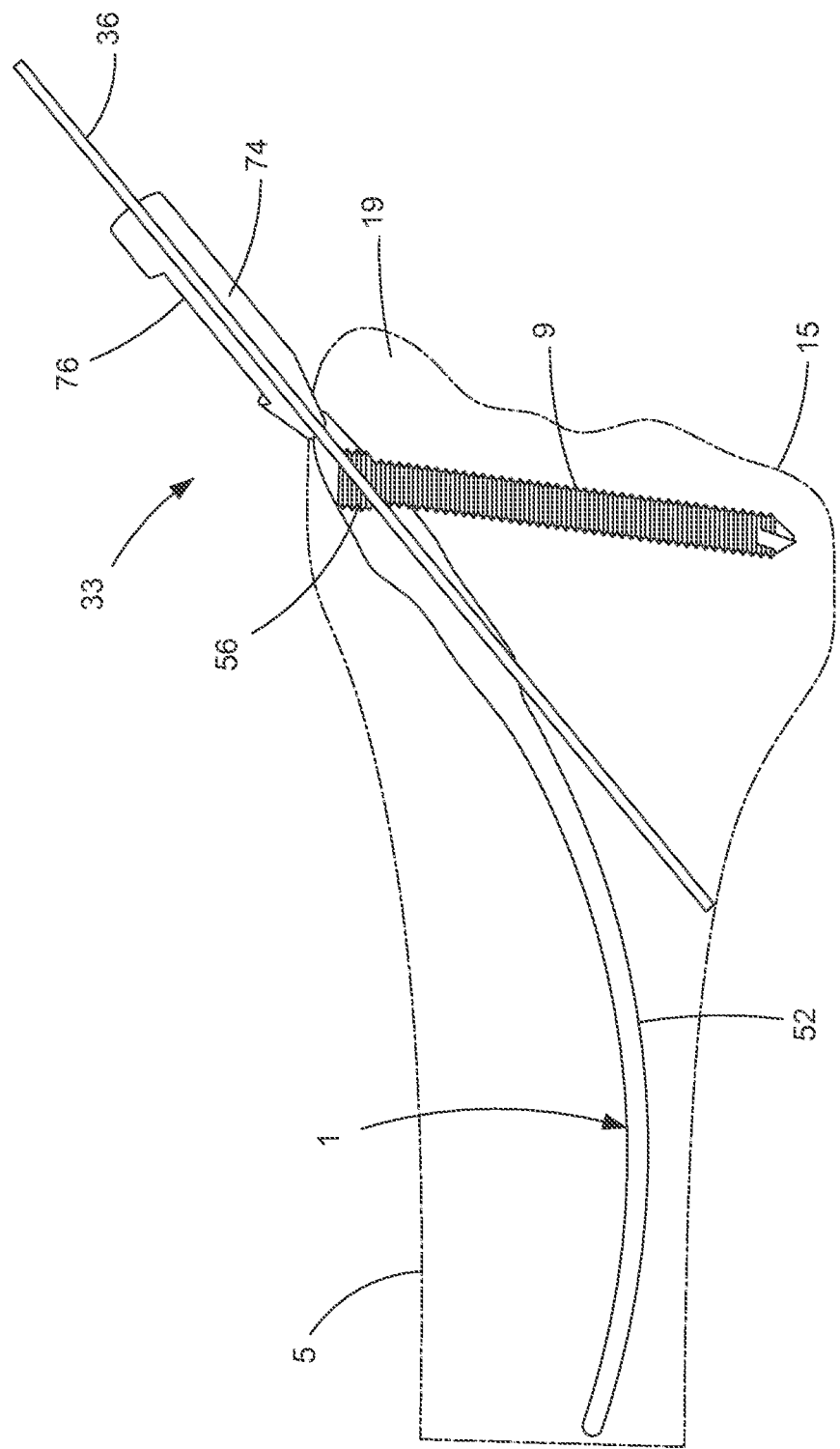

Referring to FIG. 5D, the intramedullary fixation system 33, for instance the insertion device 30, can further include a measuring device 38 configured to measure the depth of insertion of a fixation element, such as a screw. The measuring device 38 that can be added to the top of the aiming arm 34 and onto the K-wire 36, in order to establish the depth of articular fragment 15 (shown to be 28 mm in accordance with the illustration) so that appropriate length screws such as the first and second screws 9 and 11 described above can be selected. Because the first and second screws 9 and 11 are configured to attach to the articular fragment 15, the first and second screws 9 and 11 can be referred to as distal screws. Next, as illustrated in FIG. 5E, the distal screws such as first and second screws 9 and 11 can be inserted over the respective K-wires 36 and through the aiming arm 34, for instance after the measuring device 38 has been removed. Next, as illustrated in FIG. 5F, the aiming arm 34 can be removed.

Figure 5H:
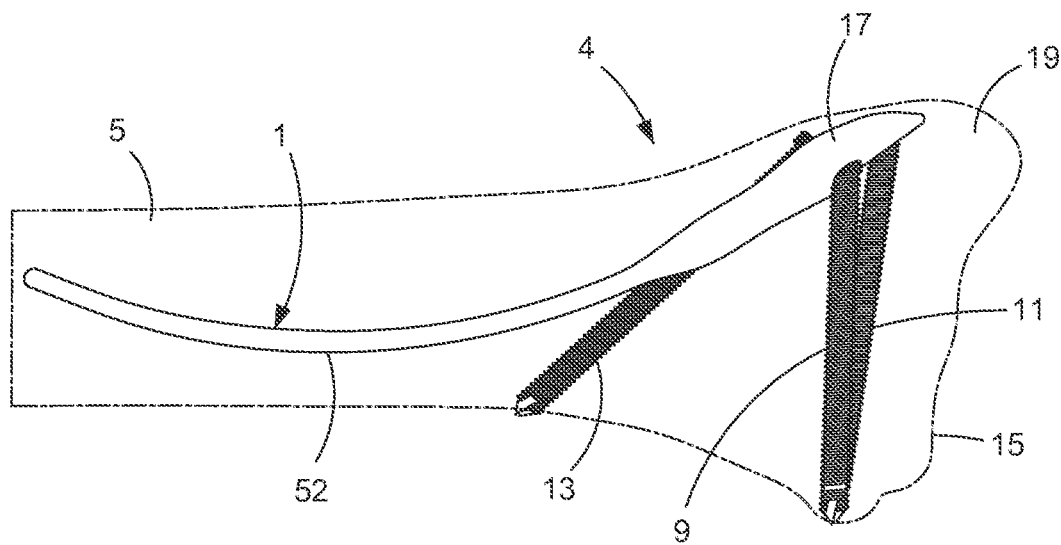
Figure 5I:
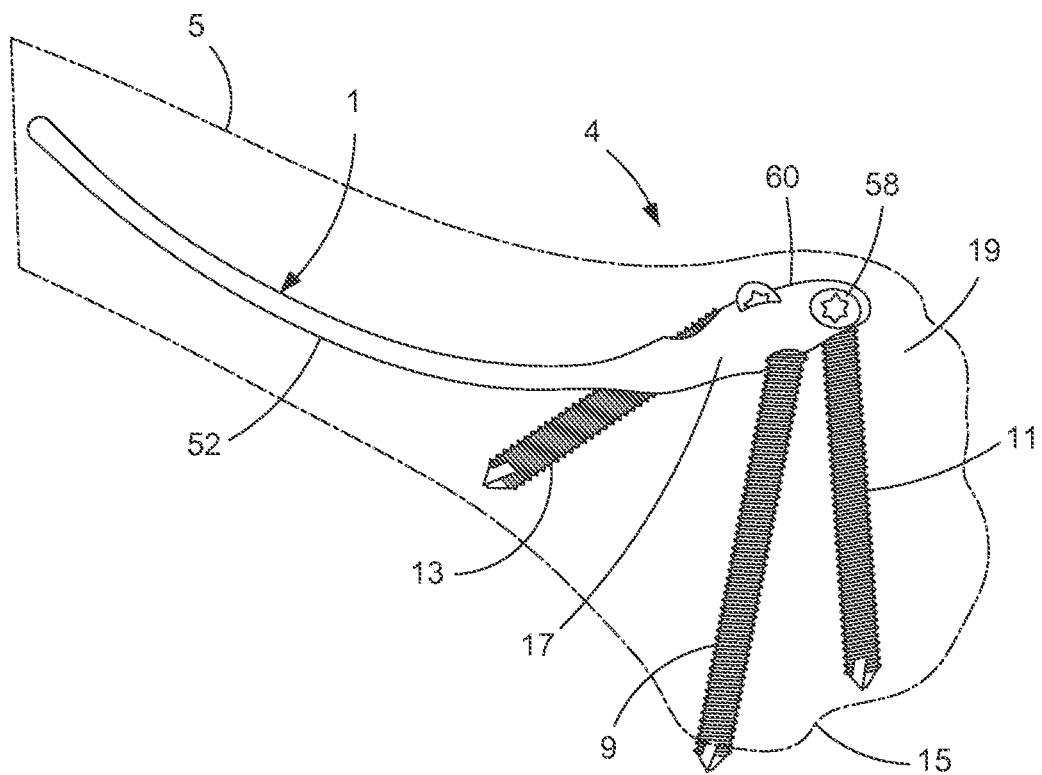
Figure 5J:
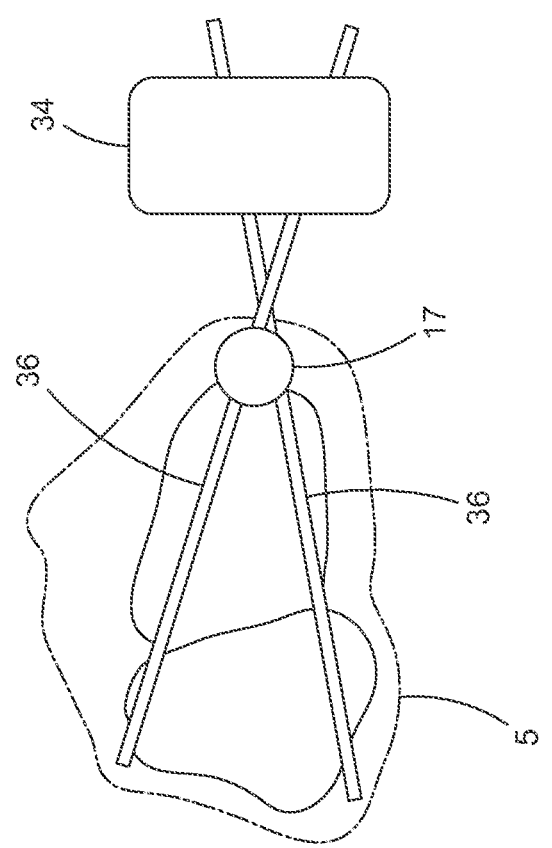

After the addition of distal screws 9 and 11, a screw such as the third screw 13 can be inserted through the opening 70 and through at least a portion of the head 17 of the intramedullary fixation device 1, as described above. For instance, referring now to FIG. 5G, the insertion instrumentation 62 can further include a K-wire sleeve 74 that also defines a measuring device 76, through which a K-wire 36 can be inserted along a trajectory that defines an insertion path for the third screw 13. The measuring device 76 can be placed onto the K-wire sleeve 74 so as to measure the insertion depth of the K-wire 36, such that an appropriately sized screw 13 can be selected as described above with respect to the measuring device 38 illustrated in FIG. 5D. Next, as illustrated in FIGS. 5H-5I, the third screw 13 can be inserted through the opening 70 and into the third channel 60 so as to extend across the fracture line as described above. Advantageously, implantation of the intramedullary fixation assembly 4 using the insertion instrumentation 62 requires only one bone hole, and a single skin incision and minimal instruments, thereby reducing complexity of the procedure, cost and trauma to the patient.

An aspect of the method of the present disclosure embodies the method of using the insertion instrumentation 62 for inserting an intramedullary fixation assembly 4 according to any of the embodiments described herein. For instance, a method of implanting an intramedullary fixation device in a medullary canal of a bone can support bone healing of a bone fracture between a first bone fragment and a second bone fragment. The method may have the steps of aligning the first and second bone fragments; making a hole in the cortical bone of the first bone fragment; passing an intramedullary fixation device through the hole, the intramedullary fixation device having a head from which a shaft extends and a plurality of fixation element receiving channels, each one of the plurality of fixation element receiving channels having an insertion point located in an insertion area defined in the head; inserting a first fixation element through an insertion point in the insertion area; and inserting a second fixation element through a different insertion point in the insertion area. A measurement may be taken before insertion of each of the first and the second fixation elements for determining the length of the fixation element to be inserted.

Figure 6A:
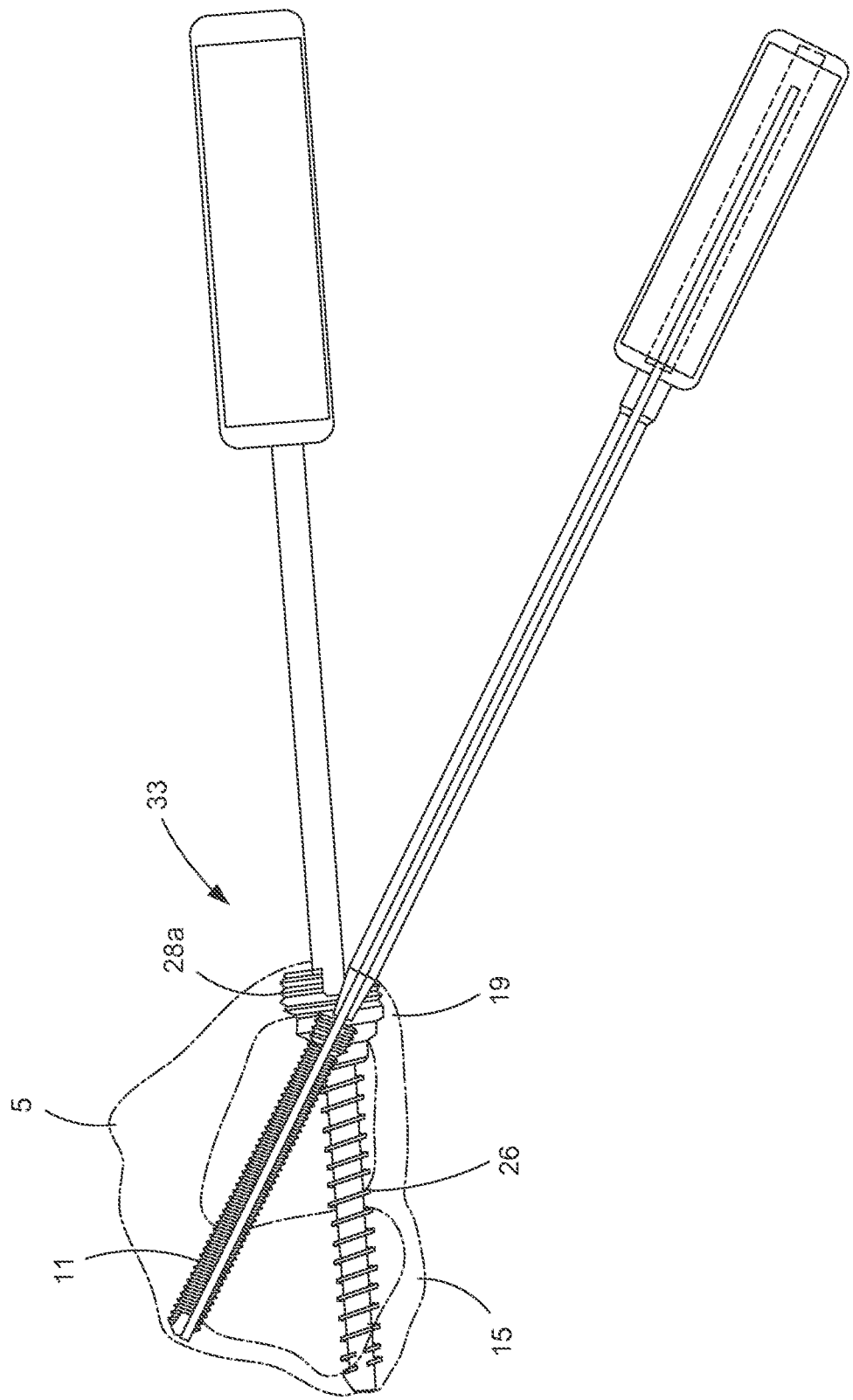
FIG. 6A shows a first step of a method of fixing a bone fracture in accordance with one embodiment.
Figure 6B:
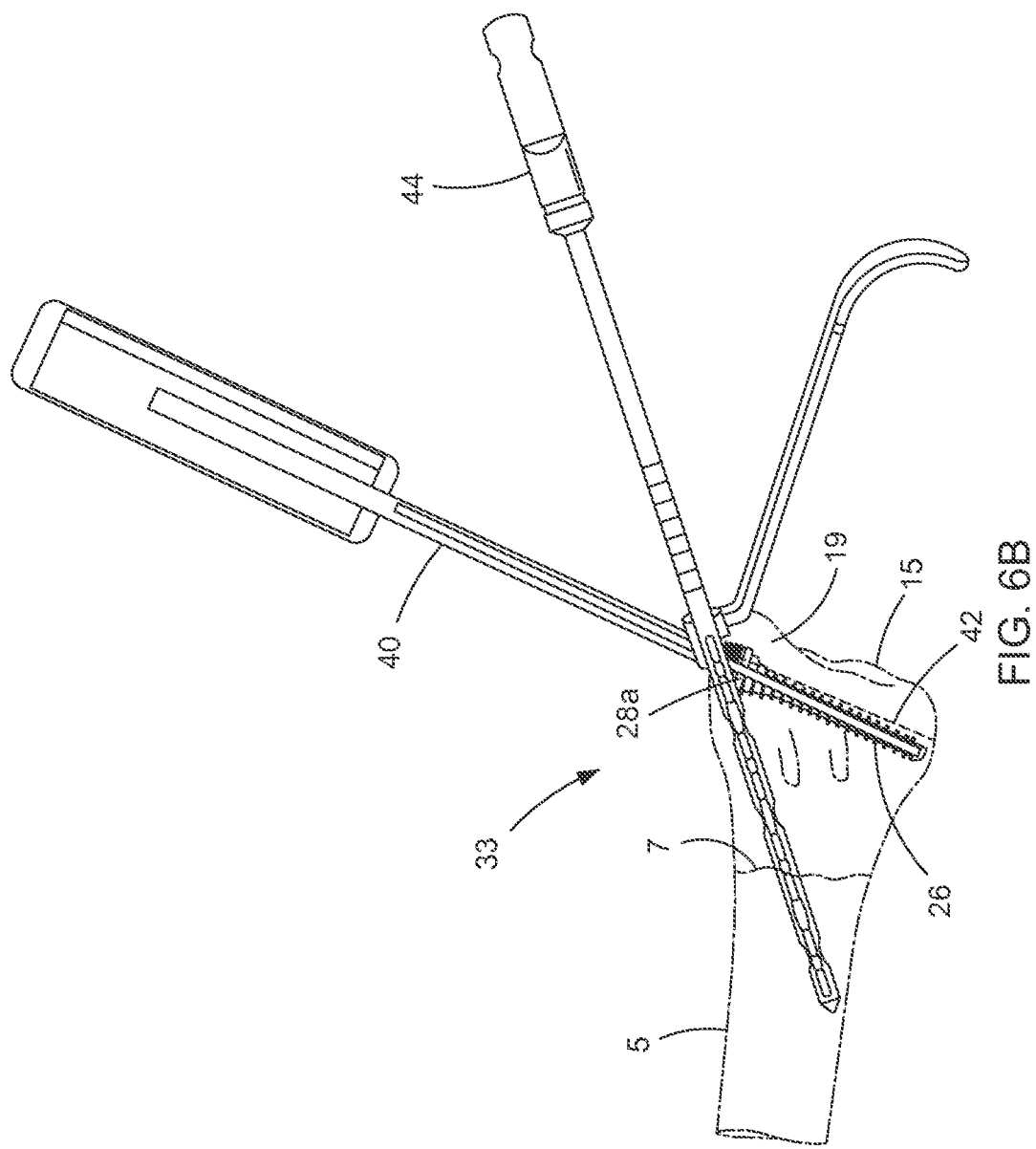
FIG. 6B shows a second step of the method of fixing a bone fracture illustrated in FIG. 6A.

FIGS. 6A and 6B illustrate certain steps of a method of fixing a bone fracture, not using the insertion device 30, for inserting an intramedullary fixation device of the present disclosure. The method may be used to insert an intramedullary fixation assembly of the type disclosed herein, such as that shown in FIGS. 4A and 4B. A 1.1 mm diameter K-wire 40 is inserted into the volar-ulnar canal 42 of the articular fragment 15 of the radius 5. A measuring device of the type described above can then placed on K-wire 40 to measure the depth of the articular fragment in order to determine the length required for first fixation element 26. The measuring device is then removed and a hole is drilled through the styloid process 19, over the K-wire 40, using a drill of any size as desired, for instance with a 2.0 mm diameter. The first fixation element 26 is then inserted in the hole. After insertion of first fixation element 26 a second K-wire 40 is inserted in the articular fragment 15 and then a hole is drilled over said K-wire. Using a measuring device on the second K-wire, the desired length of a second fixation element, such as the second screw 11, is obtained. The measuring device is then removed and the second screw 11 is inserted into the drilled hole. FIG. 6B illustrates this step in the procedure, viewed down the length of radius 5 from the end of articular fragment 15. Following insertion of the second screw 11, a hole for the intramedullary fixation device 24 is drilled through styloid process 19. Because the second screw 11 is configured to be anchored to the articular fragment 15, the second screw 11 can be referred to as a distal screw. A length is measured to establish the desired length of the intramedullary fixation device 24 using a measuring device 44, which can be configured as described above with respect to FIGS. 5A-I. The measuring part 44 is then removed and the intramedullary fixation device 1 is inserted into the hole.

It will be appreciated that this description is by way of example only; alterations and modifications may be made to the described embodiments without departing from the scope of the invention as defined in the claims.

What is claimed is:

1. A styloid intramedullary fixation device dimensioned to lie within a medullary canal of a distal radius when implanted, the styloid intramedullary fixation device comprising:
   a) a curvilinear body having a head portion and an end opposite the head portion, the curvilinear body elongate along a central axis from the head portion to the end such that the central axis lies in a first plane;
   b) a first insertion channel configured to accept a first bone screw, the first insertion channel having a first channel insertion point located at the head portion, a first channel exit point from the curvilinear body, and a first channel axis that extends centrally through the first channel insertion point and the first channel exit point such that, as the central axis extends in a direction from the head portion to the end, the central axis converges with the first channel axis at a select side of the first channel axis, then is tangent to the first channel axis at a tangent location, and then diverges from the first channel axis at the select side; and
   c) a second insertion channel configured to accept a second bone screw, the second insertion channel having a second channel insertion point located at the head portion, a second channel exit point located at the head portion, and a second channel axis that extends centrally,
   wherein the tangent location is disposed between the end and the second channel axis on a second plane that extends through the end, the tangent location, and the second channel axis, and the styloid intramedullary fixation device is devoid of an insertion channel that is configured to accept a bone screw and that has an exit point that is positioned closer to the end than the first channel exit point is positioned to the end.

2. The styloid intramedullary fixation device of claim 1, wherein the central axis, the first channel axis, and the second channel axis each diverge with respect to each other.

3. The styloid intramedullary fixation device of claim 2, wherein the head portion comprises an insertion area and wherein the first and second channel insertion points are located within the insertion area.

4. The styloid intramedullary fixation device of claim 1, further comprising a third insertion channel configured to accept a third bone screw, the third insertion channel having a third channel insertion point located at the head portion, a third channel exit point located at the head portion, and a third channel axis that extends centrally through the third channel insertion point and the third channel exit point.

5. The styloid intramedullary fixation device of claim 4, wherein the third channel axis diverges from the first plane in the direction from the head portion to the end.

6. The styloid intramedullary fixation device of claim 4, wherein the central axis, the first channel axis, the second channel axis, and the third channel axis each diverge with respect to each other.

7. The styloid intramedullary fixation device of claim 4, wherein the curvilinear body includes an upper surface and a lower surface opposite the upper surface, each of the upper surface and the lower surface extends from the head portion to the end, and a third plane that includes the first channel axis intersects both the second channel axis and the third channel axis at respective locations between the upper surface and the lower surface.

8. The styloid intramedullary fixation device of claim 1, wherein the first channel axis is substantially coextensive with the central axis.

9. The styloid intramedullary fixation device of claim 1, wherein the curvilinear body includes an upper surface and a lower surface opposite the upper surface, each of the upper surface and the lower surface extends from the head portion to the end, and the tangent location is between the upper surface and the lower surface.

10. A styloid intramedullary nail dimensioned to lie within a medullary canal of a distal radius when implanted, the styloid intramedullary fixation nail comprising:
(a) a rigid curvilinear body elongate along a central axis of the styloid intramedullary fixation nail, the curvilinear body having a head portion and a shaft portion terminating in an end opposite the head portion, the head portion defining a first width that is measured along a straight line perpendicular to the central axis, and the shaft portion defining a second width that is measured along a straight line perpendicular to the central axis and that is less than the first width, the central axis extending along a length of the body from the head portion to the end such that the central axis lies in a first plane, the head portion of the body defining a proximal surface transverse to the central axis at a proximal end of the body;
(b) a first insertion channel having a first channel insertion point extending into the curvilinear body via the proximal surface of the head portion of the body and a first channel exit point from the curvilinear body, the first insertion channel configured to accept a first bone screw, the first insertion channel defining a first channel axis that extends centrally through the first channel insertion point and the first channel exit point such that the first channel axis intersects the central axis at a first point and a second point spaced from the first point along the length of the body; and
(c) a second insertion channel having a second channel insertion point into the curvilinear body and a second channel exit point from the curvilinear body, the second insertion channel configured to accept a second bone screw, the second insertion channel defining a second channel axis that extends centrally through the second channel insertion point and the second channel exit point, the second channel insertion point and exit point located within the head portion;
wherein the second channel axis diverges from the first plane, and the first channel axis diverges from a second plane that is orthogonal to the first plane.

11. The styloid nail of claim 10, wherein the first channel axis is substantially coextensive with the central axis.

12. The styloid nail of claim 10, wherein the second channel axis diverges from the first plane at a second channel axis angle of at least 5°, and the first channel axis diverges from the second plane at a first channel axis angle of at least 20°.

13. The styloid nail of claim 12, wherein the second channel axis angle is at least 10°.

14. The styloid nail of claim 13, wherein the first channel axis angle is at least 30°.

15. The styloid nail of claim 14, further comprising a third insertion channel having a third channel insertion point into the curvilinear body and a third channel exit point from the curvilinear body, the third insertion channel configured to accept a third bone screw, the third insertion channel defining a third channel axis that extends centrally through the third channel insertion point and the third channel exit point, the third channel insertion point and exit point located within the head portion.

16. The styloid nail of claim 15, wherein the third channel axis diverges from the first plane at an angle of at least 5°.

17. The styloid nail of claim 10, wherein the curvilinear body has a rigidity sufficient to stably reduce a bone fracture and restrict motion of the portions of the bone in a plurality of dimensions.

18. The styloid nail of claim 10, wherein the curvilinear body has a rigidity sufficient to restrict motion of the portions of the bone in six dimensions.

* * * * *